United States Patent
Saint et al.

(10) Patent No.: US 9,959,391 B2
(45) Date of Patent: *May 1, 2018

(54) MEDICINE ADMINISTERING SYSTEM INCLUDING INJECTION PEN AND COMPANION DEVICE

(71) Applicant: Companion Medical, Inc., San Diego, CA (US)

(72) Inventors: Sean Saint, San Diego, CA (US); Arnold Holmquist, Temecula, CA (US); Cory McCluskey, Encinitas, CA (US); Jack Pryor, Ladera Ranch, CA (US); Jasper Benke, San Diego, CA (US)

(73) Assignee: Companion Medical, Inc., San Diego, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/613,851

(22) Filed: Jun. 5, 2017

(65) Prior Publication Data

US 2017/0270276 A1 Sep. 21, 2017

Related U.S. Application Data

(63) Continuation of application No. 14/797,044, filed on Jul. 10, 2015, now Pat. No. 9,672,328.

(Continued)

(51) Int. Cl.
*A61M 5/142* (2006.01)
*G06F 19/00* (2018.01)
(Continued)

(52) U.S. Cl.
CPC ..... *G06F 19/3468* (2013.01); *A61M 5/31528* (2013.01); *G06F 19/3462* (2013.01);
(Continued)

(58) Field of Classification Search
CPC .. A61M 2005/3126; A61M 2005/3142; A61M 5/24; A61M 5/31551;
(Continued)

(56) References Cited

U.S. PATENT DOCUMENTS 1,955,303 A 4/1934 Lewis
4,498,904 A 2/1985 Turner et al.
(Continued)

FOREIGN PATENT DOCUMENTS

EP 0298067 4/1989
EP 513128 11/1992
(Continued)

OTHER PUBLICATIONS

Openheaver, B. R., Authorized Officer, ISA/US, International Search Report and Written Opinion, International Application No. PCT/US2014/056336, dated Dec. 31, 2014, 10 pages.

(Continued)

*Primary Examiner* — Laura Bouchelle
(74) *Attorney, Agent, or Firm* — Perkins Coie LLP

(57) ABSTRACT

Methods, systems, and devices are disclosed for administering a medicament to a patient. In one aspect, a system includes an injection pen device in wireless communication with a mobile communication device. The injection pen device includes a housing including a chamber to encase a cartridge containing medicine, a dose setting and dispensing mechanism to set the mechanism to dispense a particular dose of the medicine from the loaded cartridge, a sensor unit to detect a dispensed dose based on positions and/or movements of the dose setting and dispensing mechanism, and an electronics unit in communication with the sensor unit to process the detected dispensed dose and time data associated with a dispensing event and to wirelessly transmit the dose data to a user's device. The mobile communication device (Continued)

provides a software application to provide the user with health information using the processed dose data.

26 Claims, 9 Drawing Sheets

Related U.S. Application Data

(60) Provisional application No. 62/162,572, filed on May 15, 2015, provisional application No. 62/022,798, filed on Jul. 10, 2014.

(51) Int. Cl.
| | |
|---|---|
| *A61M 5/315* | (2006.01) |
| *H04B 7/24* | (2006.01) |
| *H04L 9/30* | (2006.01) |
| *H04L 9/08* | (2006.01) |
| *A61M 5/31* | (2006.01) |

(52) U.S. Cl.
CPC .......... *H04B 7/24* (2013.01); *A61M 5/31525* (2013.01); *A61M 5/31545* (2013.01); *A61M 5/31565* (2013.01); *A61M 5/31566* (2013.01); *A61M 5/31568* (2013.01); *A61M 2005/14208* (2013.01); *A61M 2005/3126* (2013.01); *A61M 2205/3584* (2013.01); *A61M 2205/52* (2013.01); *H04L 9/08* (2013.01); *H04L 9/30* (2013.01)

(58) Field of Classification Search
CPC .......... A61M 5/31528; A61M 5/31545; A61M 2205/3592; A61M 2205/3553; A61M 2205/3561; A61M 2205/3569; A61B 5/14532
See application file for complete search history.

(56) References Cited

U.S. PATENT DOCUMENTS

| | | | |
|---|---|---|---|
| 4,515,584 A * | 5/1985 | Abe | A61M 5/1723 |
| | | | 417/477.1 |
| 4,950,216 A | 8/1990 | Weder | |
| 4,973,318 A | 11/1990 | Holm et al. | |
| 5,279,586 A | 1/1994 | Balkwill | |
| 5,626,566 A | 5/1997 | Petersen et al. | |
| 5,681,285 A | 10/1997 | Ford et al. | |
| 5,925,021 A | 7/1999 | Castellano et al. | |
| 5,984,900 A | 11/1999 | Mikkelsen | |
| 6,004,297 A | 12/1999 | Steenfeldt-Jensen et al. | |
| 6,042,571 A | 3/2000 | Hjertman et al. | |
| 6,235,004 B1 | 5/2001 | Steenfeldt-Jensen et al. | |
| 6,302,855 B1 | 10/2001 | Lav et al. | |
| 6,482,185 B1 | 11/2002 | Hartmann | |
| 6,817,986 B2 | 11/2004 | Slate et al. | |
| 8,221,356 B2 | 7/2012 | Enggard et al. | |
| RE43,834 E | 11/2012 | Steenfeldt-Jensen et al. | |
| 9,672,328 B2 * | 6/2017 | Saint | A61M 5/31528 |
| 2003/0065536 A1 | 4/2003 | Hansen et al. | |
| 2004/0039255 A1 | 2/2004 | Simonsen et al. | |
| 2005/0038674 A1 | 2/2005 | Braig et al. | |
| 2005/0049179 A1 | 3/2005 | Davidson et al. | |
| 2005/0182358 A1 | 8/2005 | Veit et al. | |
| 2005/0192494 A1 | 9/2005 | Ginsberg | |
| 2006/0173417 A1 | 8/2006 | Rosen et al. | |
| 2007/0021715 A1 | 1/2007 | Kohlbrenner et al. | |
| 2007/0186923 A1 | 8/2007 | Poutiatine et al. | |
| 2007/0239486 A1 | 10/2007 | Gordon | |
| 2008/0162192 A1 | 7/2008 | Vonk et al. | |
| 2008/0188813 A1 | 8/2008 | Miller et al. | |
| 2008/0201169 A1 | 8/2008 | Galasso et al. | |
| 2008/0234663 A1 | 9/2008 | Yodfat et al. | |
| 2008/0235053 A1 | 9/2008 | Ray et al. | |
| 2009/0036771 A1 | 2/2009 | Fago et al. | |
| 2009/0048561 A1 | 2/2009 | Burren et al. | |
| 2009/0069742 A1 | 6/2009 | Larsen | |
| 2009/0163793 A1 * | 6/2009 | Koehler | A61B 5/0002 |
| | | | 600/365 |
| 2009/0209938 A1 | 8/2009 | Aalto-Setala | |
| 2010/0081993 A1 | 4/2010 | O'Connor | |
| 2011/0264033 A1 * | 10/2011 | Jensen | A61M 5/1452 |
| | | | 604/65 |
| 2011/0275986 A1 | 11/2011 | Bashan | |
| 2011/0313349 A1 | 12/2011 | Krulevitch et al. | |
| 2011/0313350 A1 * | 12/2011 | Krulevitch | A61M 5/24 |
| | | | 604/65 |
| 2012/0072236 A1 | 3/2012 | Atkin | |
| 2013/0171938 A1 | 7/2013 | Mears et al. | |
| 2013/0184996 A1 | 7/2013 | Zivitz et al. | |
| 2013/0197445 A1 | 8/2013 | Schabbach et al. | |
| 2013/0197479 A1 | 8/2013 | Butler et al. | |
| 2013/0211248 A1 | 8/2013 | Cowan et al. | |
| 2013/0291116 A1 * | 10/2013 | Homer | G06F 21/00 |
| | | | 726/26 |
| 2014/0276531 A1 * | 9/2014 | Walsh | G06F 19/3468 |
| | | | 604/500 |
| 2016/0012205 A1 | 1/2016 | Saint | |
| 2016/0030683 A1 * | 2/2016 | Taylor | A61M 5/14248 |
| | | | 604/151 |
| 2017/0068799 A1 | 3/2017 | Mensinger | |

FOREIGN PATENT DOCUMENTS

| | | |
|---|---|---|
| EP | 927057 | 7/1999 |
| EP | 2572740 | 3/2013 |
| WO | 9638190 | 12/1996 |
| WO | 2010052275 | 5/2010 |
| WO | 2011041007 | 4/2011 |
| WO | 2013053695 | 4/2013 |
| WO | 2014128157 | 8/2014 |

OTHER PUBLICATIONS

Young, Lee W., ISA/US, International Search Report, International Application No. PCT/US15/40089, dated Dec. 22, 2015, 13 pages.

Young, Lee W., ISA/US, Invitation to Pay Additional Fees and Partial Search Report, International Application No. PCT/US15/40069, dated Oct. 1, 2015, 2 pages.

Extended European Search Report for European Patent Application No. 14849422.2, dated May 4, 2017, 11 pages.

* cited by examiner

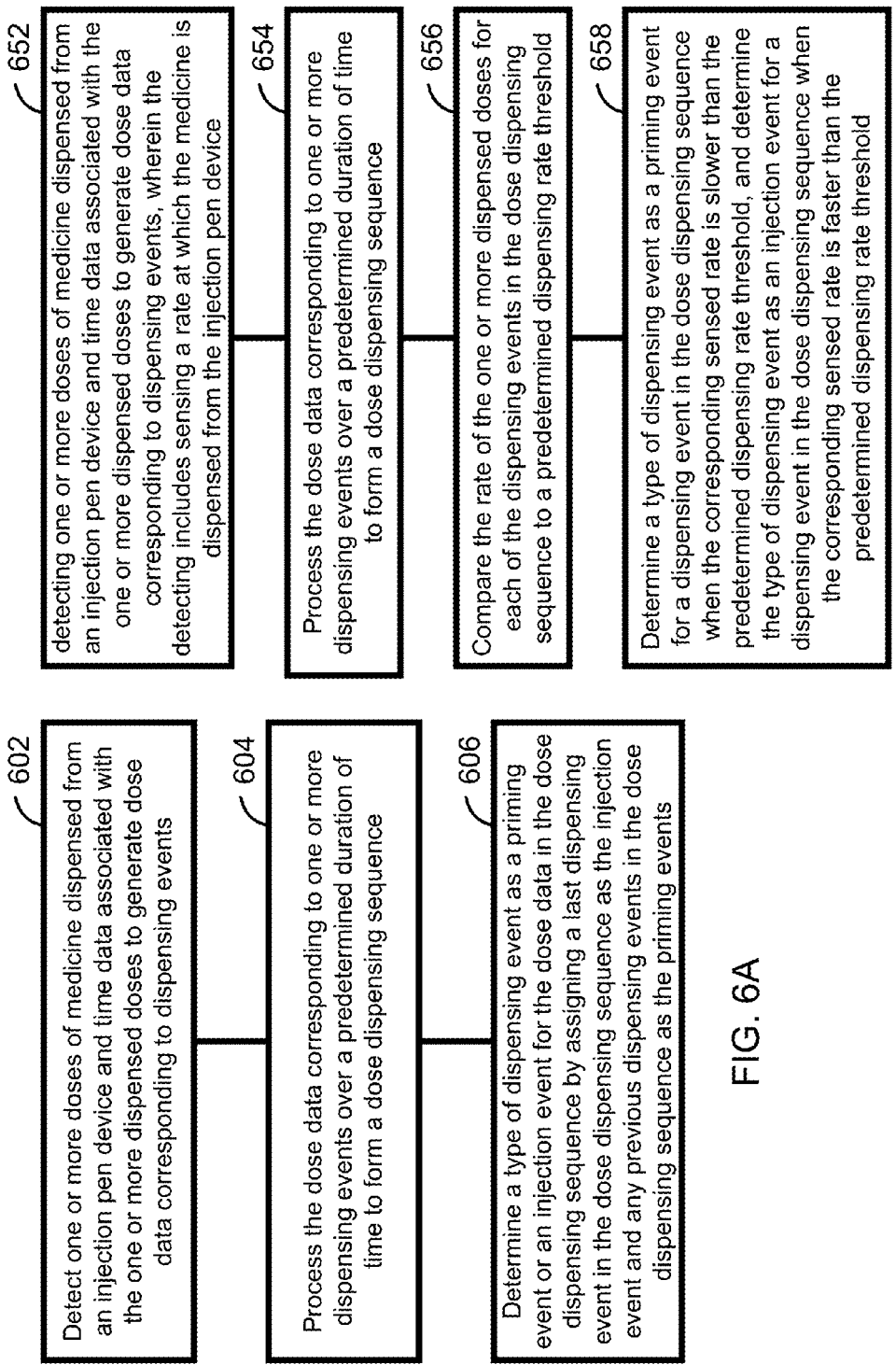

MEDICINE ADMINISTERING SYSTEM INCLUDING INJECTION PEN AND COMPANION DEVICE

CROSS-REFERENCE TO RELATED APPLICATIONS

This patent document is a continuation of U.S. application Ser. No. 14/797,044 entitled "MEDICINE ADMINISTERING SYSTEM INCLUDING INJECTION PEN AND COMPANION DEVICE" filed on Jul. 10, 2015, which claims priorities to and benefits of U.S. Provisional Patent Application No. 62/022,798 entitled "SYSTEM FOR ADMINISTERING A MEDICAMENT" filed on Jul. 10, 2014, and U.S. Provisional Patent Application No. 62/162,572 entitled "MEDICINE ADMINISTERING SYSTEM INCLUDING INJECTION PEN AND COMPANION DEVICE" filed on May 15, 2015. The entire content of the above patent applications is incorporated by reference as part of the disclosure of this patent document.

TECHNICAL FIELD

This patent document relates to medicine administering systems, devices, and processes.

BACKGROUND

Diabetes mellitus, also referred to as diabetes, is a metabolic disease associated with high blood sugar due to insufficient production or use of insulin by the body. Diabetes is widely-spread globally, affecting hundreds of millions of people, and is among the leading causes of deaths globally. Diabetes has been categorized into three categories or types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. The third type of diabetes is commonly referred to as gestational diabetes, which can occur during pregnancy when a pregnant woman develops a high blood glucose level. Gestational diabetes can develop into type 2 diabetes, but often resolves after the pregnancy.

SUMMARY

Systems, devices, and techniques are disclosed for administering medicine to patients and providing health management capabilities for patients and caregivers.

In one aspect, a system for administering a medicine to a patient includes an injection pen device and a mobile communication device in wireless communication with the injection pen. The injection pen device includes a housing including a main body structured to include a chamber to encase a cartridge containing medicine when the cartridge is loaded in the chamber, a dose setting and dispensing mechanism to set and dispense a particular dose of the medicine from the loaded cartridge, the dose setting and dispensing mechanism including a dose knob, a shaft, and a piston assembly including a plunger, in which the dose knob is rotatable to cause the shaft to move to a position proportional to a set dose of the medicine, and in which the dose knob is translationally moveable to cause the shaft to drive the plunger to push against the cartridge to dispense the medicine from the cartridge, a sensor unit to detect a dispensed dose based on one or both of positions and movements of the dose setting and dispensing mechanism, in which the dispensed dose includes an amount of medicine dispensed from the cartridge, and an electronics unit in communication with the sensor unit, the electronics unit including a processing unit including a processor and memory to process the detected dispensed dose and time data associated with a dispensing event to generate dose data, a transmitter to wirelessly transmit the dose data to a user's device, and a power source to provide electrical power to the electronics unit. The mobile communication device includes a data processing unit including a processor to process the dose data and a memory to store or buffer the dose data, a display to present a user interface to the user, and a wireless communications unit to wirelessly receive the dose data from the injection pen device.

In one aspect, a method to classify a dose of medicine dispensed from an injection pen includes detecting one or more doses of medicine dispensed from an injection pen device and time data associated with the one or more dispensed doses to generate dose data corresponding to dispensing events; processing the dose data corresponding to one or more dispensing events over a predetermined duration of time to form a dose dispensing sequence; and determining a type of dispensing event as a priming event or an injection event for the dose data in the dose dispensing sequence by assigning a last dispensing event in the dose dispensing sequence as the injection event and any previous dispensing events in the dose dispensing sequence as the priming events.

In one aspect, a method to classify a dose of medicine dispensed from an injection pen includes detecting one or more doses of medicine dispensed from an injection pen device and time data associated with the one or more dispensed doses to generate dose data corresponding to dispensing events, in which the detecting includes sensing a rate at which the medicine is dispensed from the injection pen device; processing the dose data corresponding to one or more dispensing events over a predetermined duration of time to form a dose dispensing sequence; comparing the rate of the one or more dispensed doses for each of the dispensing events in the dose dispensing sequence to a predetermined dispensing rate threshold; and determining a type of dispensing event as a priming event for a dispensing event in the dose dispensing sequence when the corresponding sensed rate is slower than the predetermined dispensing rate threshold, and determining the type of dispensing event as an injection event for a dispensing event in the dose dispensing sequence when the corresponding sensed rate is faster than the predetermined dispensing rate threshold.

In one aspect, a method of unbonding an injection pen device from a mobile communication device includes providing instructions to a user of the injection pen device that has been communicatively bonded to a first mobile communication device to perform an operation sequence including two or more operations of the injection pen device in a predetermined time frame; initiating, by a processing unit of the injection pen device, a count of the predetermined time frame once a dose setting mechanism of the injection pen device is set at or greater than a first level; detecting, by the injection pen device, operations of the dose setting and a dose dispensing mechanism of the injection pen device; and clearing encryption keys stored in the processing unit of the injection pen device associated with the first mobile communication device when the operation sequence is detected within the predetermined time.

In some aspects, an intelligent medicine administration system includes a medicine injection device, in communication with a patient's companion device (e.g., smartphone), in which the injection device is able to detect and record dose sizes that are dispensed (e.g., primed or injected to the patient), and to distinguish between a prime dose and a therapy dose. The companion device can include a software application having a dose calculator that can suggest the dose the patient should set on the injection device, and provides control over several functionalities of the injection device (e.g., safety lock, assisted by the dose distinguisher). Multiple embodiments of the injection device include various features, including a sensor to detect when the device is being operated, a sensor to detect the dose setting, a sensor to monitor temperature of the injection device, data processing, storage and communication capabilities, and control and messaging (e.g., alert) features to affect the patient's operation of the device.

The intelligent medicine administration system of the present technology is also capable of keeping track of doses that have been administered. In some implementations, for example, a method of tracking usage of a medicament by a patient through a pen device, where the medicament is administered from the pen in a plurality of boluses over time, is provided. In this method, information is recorded about the medicament administration and the information is stored on a companion device. In some embodiments, for example, the information comprises the quantity and time of each administered bolus of the medicament. The pen and companion device are in communication and allow the patient to use the pen to deliver one or more boluses with the pen, in which the pen can automatically store information associated with each delivered bolus, e.g., including at a minimum the amount of the bolus and the time at which the bolus was delivered, and/or determine the time related information with the bolus, and transmit that information to the companion device.

Medication tracking systems are needed in critical care and ambulance environments, for example, where continuity of medication tracking across health care teams is needed. In this case, a patient record of dosing could be transferred with the patient from one care team (e.g. paramedics) to a second care team (e.g. ER staff). This information could be transferred by transferring a device with the patient or sending the data to the cloud based medical record for the patient, for example.

BRIEF DESCRIPTION OF THE DRAWINGS

FIGS. 6A and 6B show diagrams of exemplary methods to classify a dose of medicine dispensed from an injection pen.

DETAILED DESCRIPTION

Figure 1A:
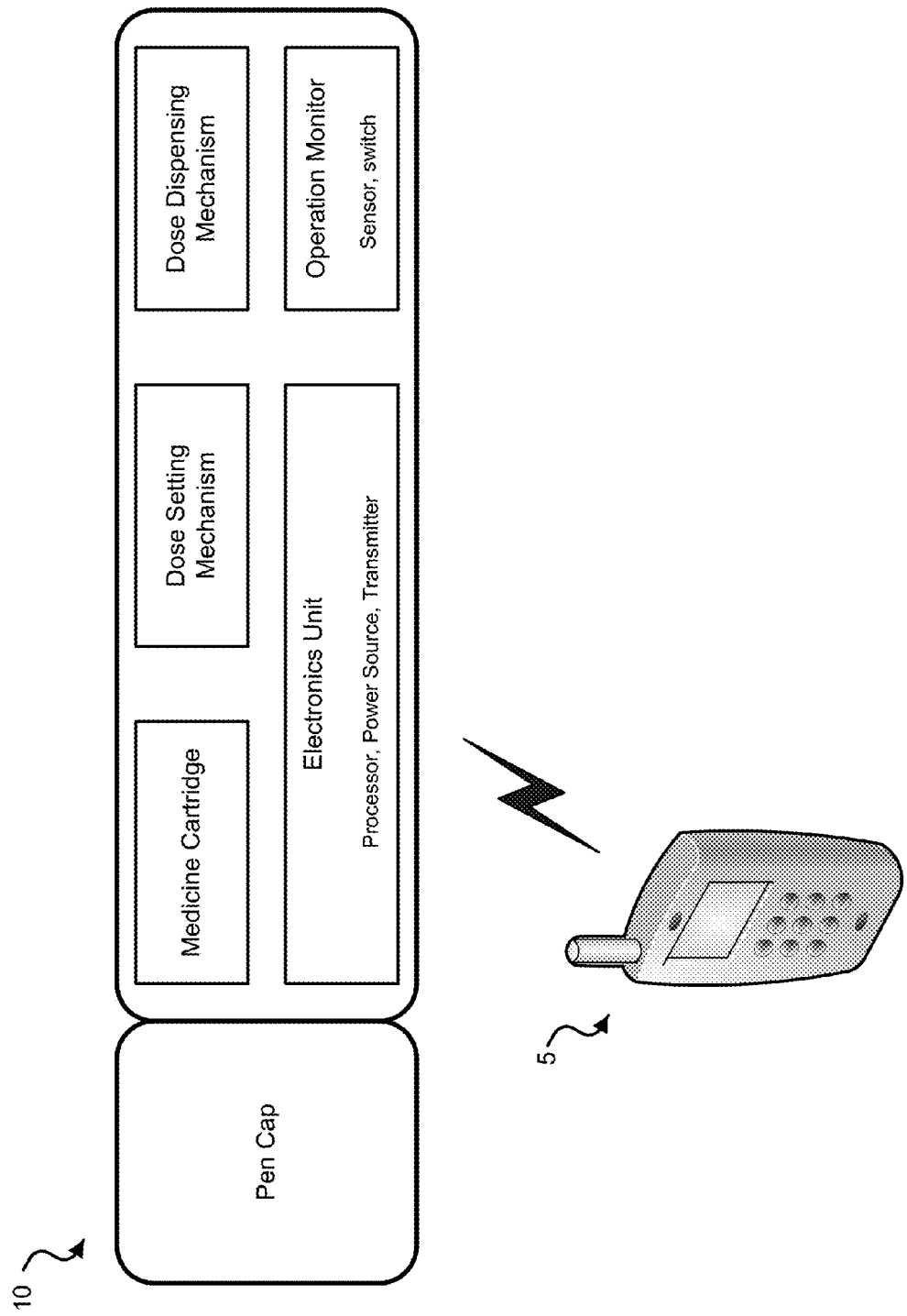
FIG. 1A shows a block diagram of an exemplary pen device of the disclosed intelligent medicine administration system.

There are many different diseases and conditions that require a patient to self-administer doses of a fluid medication. Typically, when administering a fluid medication, the appropriate dose amount is set and dispensed by the patient using a syringe, a pen, or a pump. For example, self-administered medicaments or medicine include insulin used to treat diabetes, Follistim® used to treat infertility, or other injectable medicines such as Humira®, Enbrel®, Lovenox® and Ovidrel®, or others.

A medicament pen, also referred to as a pen, is a device that can be used to inject a quantity of a medicine (e.g., single or multiple boluses or doses of the medicine) into a user's body, where more than one dose can be stored in a medicine cartridge contained in the pen device. Pens offer the benefit of simplicity over other methods of delivery, such as syringe or pump based methods. For example, syringes typically require more steps to deliver a dose, and pumps typically are more complicated to use and require a constant tether to the patient. However, previously there has been no automated way to track and communicate the doses given with the pen in a simple manner. In addition, it can be difficult to know how much to dose, when to dose, or if the patient dosed at all.

As with the dosing of any medication, it is sometimes hard to remember if a dose has been given. For this reason pill reminders have been developed where the patient places the medication for the day in a cup labeled with that day. Once they take their medication there is no question it has been taken because the pills are no longer in the cup. Yet, there are no widely acceptable solutions that address this problem for injection-based therapies.

Disclosed are intelligent medicine administering systems to provide health management capabilities for patients and caregivers. In some aspects, a system includes a medicine injection device, in communication with a patient's companion device (e.g., smartphone), in which the injection device is able to detect and record dose sizes that are dispensed (e.g., primed or injected to the patient), and to distinguish between a prime dose and a therapy dose. The companion device can include a software application having a dose calculator that can suggest the dose the patient should set on the injection device, and provides control over several functionalities of the injection device (e.g., safety lock, assisted by the dose distinguisher, and pen and companion device bonding, among other functionalities). Multiple embodiments of the injection device include various features, including a sensor to detect when the device is being operated, a sensor to detect the dose setting, a sensor to monitor temperature of the injection device, data processing, storage and communication capabilities, and control and messaging (e.g., alert) features to affect the patient's operation of the device.

Communication between the pen device and the companion device provides the ability for dose tracking, logging, calculation and communication of dose data with a user, and other advantages of the intelligent medicine administering system. For example, each bolus that is dispensed by the pen device can be automatically logged and communicated to the companion device.

FIG. 1A shows a block diagram of an exemplary embodiment of a pen device 10 of the disclosed intelligent medicine administering system. The pen 10 is structured to have a body which contains the medicine cartridge (e.g., which can be replaceable), and to include a mechanism to dispense (e.g., deliver) the medicine, a mechanism to select or set the dose to be dispensed, a mechanism to determine that the device is being operated and/or to monitor the operation of the dose being dispensed (e.g., such as a switch and/or sensor, or an encoder), and an electronics unit that can include a processor, a memory, a battery or other power source, and a transmitter.

The pen 10 is configured in communication with a user's mobile computing and communication device 5, e.g., such as the user's smartphone, tablet, and/or wearable computing device, such as a smartwatch, smartglasses, etc., and/or a user's laptop and/or desktop computer, a smart television, or network-based server computer.

In some implementations of the disclosed medicine administering system, for example, to use the pen 10, the user first dials up a dose using a dose knob. The dose knob of the pen 10 can be included as part of the dose setting mechanism and/or the dose dispensing mechanism. For example, the dose may be adjusted up or down prior to administration of the dose. When the user applies a force against a dose dispensing button (e.g., presses against the dose dispensing button that is caused to protrude outward from the pen's body upon dialing the dose using the dose knob), a pushing component (e.g., also referred to as a 'plunger') of the dose dispensing mechanism is depressed against an abutment of the medicine cartridge loaded in the pen 10 to cause the pen 10 to begin to dispense the medicine, in which the quantity dispensed is in accordance with that set by the dose setting mechanism. In such implementations, the operations monitoring mechanism of the pen 10 will begin to sense movement of a rotating component or shaft that drives the plunger, for example, in which the movement is sensed through an encoder. In some examples, the encoder can be configured to sense the rotation of a component that is coupled to the drive shaft, and as the drive shaft rotates it moves linearly; and therefore by sensing rotation of the component, the movement of the drive shaft and the plunger is sensed. Movement of the encoder may be detected as data processed by a processor of the electronics unit of the pen 10, which can be used to measure the dose. In some implementations, the processor can then store the size of the dose along with a time stamp for that dose. In some implementations, the pen 10 can then transmit the dose and related information to the companion device 5. In such implementations when the dose is transmitted, the data associated with the particular transmitted dose is marked in the memory of the pen 10 as transmitted. In such implementations if the dose was not yet transmitted to the companion device 5, then the data associated with the dose will be transmitted at the next time a successful communication link between the pen 10 and the companion device 5 is established.

The dose setting mechanism of the pen 10 can include a sensor that can utilize any method of sensing rotary or linear movement. Non-limiting examples of such sensors include rotary and linear encoders, Hall effect and other magnetic based sensors, linearly variable displacement transducers, or any other appropriate method of sensing known in the art.

The dose dispensing mechanism of the pen 10 can include a manually powered mechanism or a motorized mechanism. In either case, a force (e.g., either produced by the patient or by an electrically-powered motor) pushes on the plunger of the dose dispensing mechanism to in turn force a receiving plunger of the medicament vial or cartridge to deliver the specific amount of the medicament. In some implementations, for example, the dose dispensing mechanism can be adjusted to deliver the dose over a different period of time. In one example, the dose dispensing mechanism can be operated such that the plunger is pushed in by an adjustable tension spring or change the speed of the motor to inject the dose over a time frame (e.g., 1 s, 5 s or other) to aid in the pain of dosing. In one example, the dose dispensing mechanism can be operated over a much longer period of time, e.g., to better match the dynamics of carbohydrates, which can be like an extended bolus with a pump.

The companion device 5 includes a software application, which when loaded on the companion device 5, provides a user interface to allow the user to manage his/her health related data. In some implementations, for example, the companion device 5 can be configured to control some functionalities of the pen device 10. In some implementations, for example, the companion device 5 includes the user's existing smartphone, tablet, or wearable computing device. In some implementations, for example, the companion device 5 is an independent portable device that the user may carry on his/her person. In one example embodiments of an independent portable companion device 5, the companion device 5 includes a data processing unit, wireless communication unit to allow the device to communicate with the pen device 10, and a display unit.

Figure 1B:
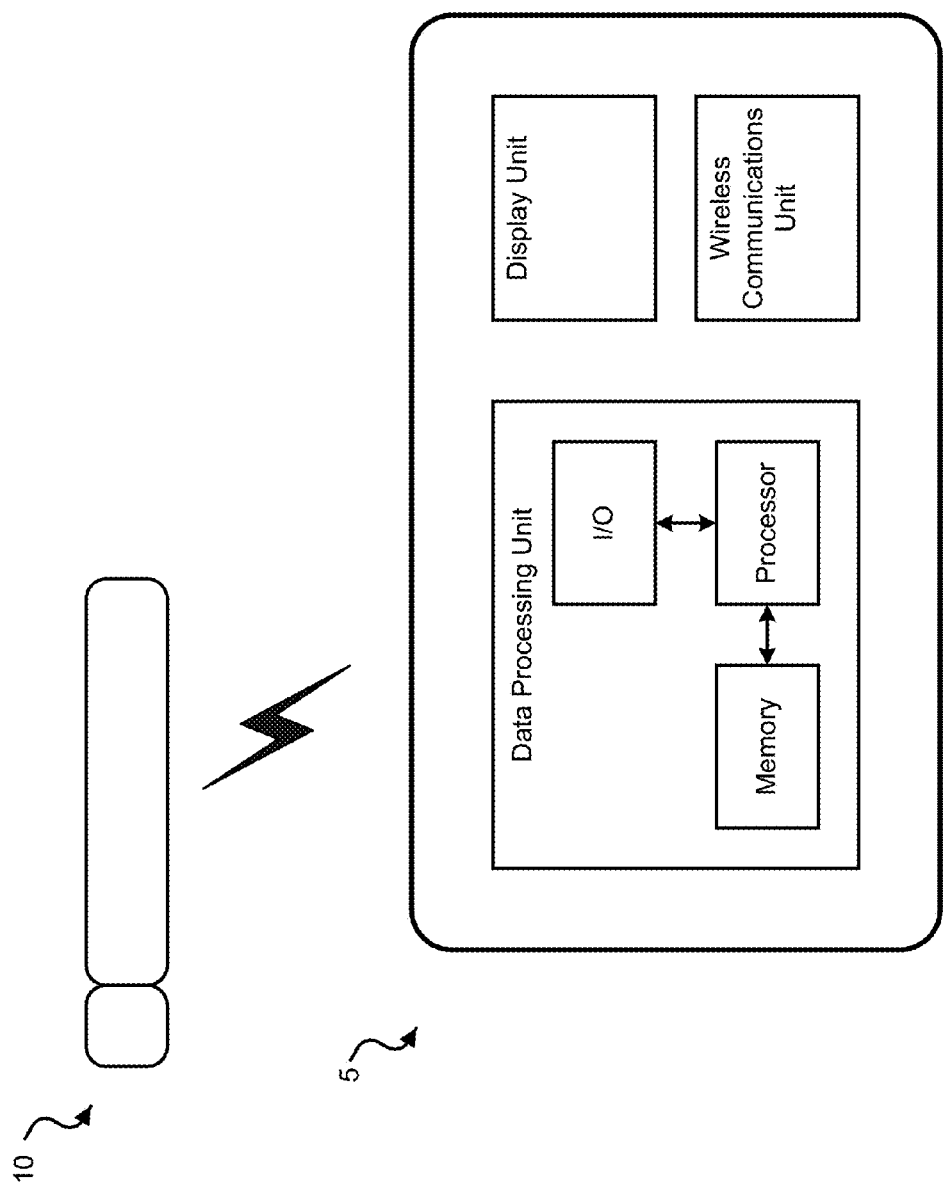
FIG. 1B shows a block diagram of an exemplary embodiment of the companion device of the disclosed intelligent medicine administering system.

FIG. 1B shows a block diagram of an exemplary embodiment of the companion device 5 of the disclosed intelligent medicine administering system. The data processing unit of the companion device 5 includes a processor to process data, a memory in communication with the processor to store data, and an input/output unit (I/O) to interface the processor and/or memory to other modules, units or devices of the companion device 5 or external devices. For example, the processor can include a central processing unit (CPU) or a microcontroller unit (MCU). For example, the memory can include and store processor-executable code, which when executed by the processor, configures the data processing unit to perform various operations, e.g., such as receiving information, commands, and/or data, processing information and data, and transmitting or providing information/data to another device. In some implementations, the data processing unit can transmit raw or processed data to a computer system or communication network accessible via the Internet (referred to as 'the cloud') that includes one or more remote computational processing devices (e.g., servers in the cloud). To support various functions of the data processing unit, the memory can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory unit. The I/O of the data processing unit can interface the data processing unit with the wireless communications unit to utilize various types of wired or wireless interfaces compatible with typical data communication standards, for example, which can be used in communications of the data processing unit with other devices such as the pen device 10, via a wireless transmitter/receiver (Tx/Rx) unit, e.g., including, but not limited to, Bluetooth, Bluetooth low energy, zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces. The I/O of the data processing unit can also interface with other external interfaces, sources of data storage, and/or visual or audio display devices, etc. to retrieve and transfer data and information that can be processed by the processor, stored in the memory unit, or exhibited on an output unit of the companion device 5 or an external device. For example, a display unit of the companion device 5 can be configured to be in data communication with the data processing unit, e.g., via the I/O, to provide a visual display, an audio display, and/or other sensory display that produces the user interface of the software application of the disclosed technology for health management. In some examples, the display unit can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

In operation of the disclosed intelligent medicine administering system, for example, when a dosing event (e.g., an amount of fluid is dispensed from the pen device 10), a time stamp associated with the dispensing is referenced is recorded by the processing unit of the pen 10 (e.g., stored in the memory of the pen 10). For example, the time stamp may be the current time or a time where a count-up timer is used. When the dose information is eventually transmitted to the companion device 5, the time stamp and/or a 'time-since-dose' parameter is transmitted by the pen 10 and received by the companion device 5 and stored in the memory of the data processing unit of the companion device 5. In some implementations, for example, the time of the dose can be determined without the pen having to know the current time. This can simplify operation and setup of the pen 10. In some implementations, for example, a user time is initialized on the pen 10 from the companion device 5, in which the user time is used for dose time tracking. Using the disclosed system, the companion device 5 can know the time of the dose relative to the current time.

Once the companion device 5 receives the dose related information (e.g., which can include the time information and dose setting and/or dispensing information, and other information about the pen 10 related to the dosing event), the companion device 5 stores the dose related information in memory, e.g., which can include among a list of doses or dosing events. For example, via the software application's user interface, the companion device 5 allows the patient to browse a list of previous doses, to view an estimate of current medicament active in the patient's body ("medicament on board") based on calculations performed by a medicine calculation module of the software application, and/or to utilize a dose calculation module of the software application to assist the patient regarding dose setting information on the size of the next dose to be delivered. For example, the patient could enter carbohydrates to be eaten, current blood sugar, and the companion device 5 would already know insulin on board. Using these parameters a suggested medicine dose (e.g., such as insulin dose), calculated by the dose calculation module, may be determined. In some implementations, for example, the companion device 5 can also allow the patient to manually enter boluses into the pen device 10 or another medicine delivery device. This would be useful if the patient was forced to use a syringe, or if the battery in the pen device 10 was depleted.

Exemplary embodiments and implementations of the disclosed intelligent medicine administering system are described.

User Settable Dose Calculator: For Example, Type 2 Diabetes Dose Calculations

In some implementations, when the medicine includes insulin for treatment of diabetes, for example, the dose calculator can be configured for patients with Type 2 diabetes. Several protocols can be used to treat such patients using the disclosed intelligent medicine administering system, including a "sliding scale" feature on the software application of the companion device 5. In an example, a sliding scale dose calculator is provided by the software app and configured to be user settable by the patient user of the companion device 5 and pen device 10 (and/or accessible and settable by a healthcare provider to the patient) to allow the patient to tailor or design the input parameters of the dose calculator to their specific needs and circumstances. In an illustrative example, some Type 2 diabetic patients might replace a specific carbohydrate input (e.g., grams or calories from carbohydrates ingested) with a 3-position switch or buttons associated with "small", "medium", and "large" meals. In such implementations, the software application provides a menu to allow a user to select from existing fields of entry (e.g., such as the 'sliding scale' of meal sizes), and/or provide suggestions for new fields to be created for the dose calculator.

Multiple Pen Devices for Multiple Medicaments: Daily Dose Calculator, Drug Confusion Alerts, and Glucagon Delivery and Calculator In some cases regarding diabetes, for example, more than one medicament may be used in the treatment of diabetes. For example, long and short acting insulins may both be taken. These insulins may both be taken one or several times throughout the day. In some implementations, the companion device 5 is configured to receive signals from two or more pen devices 10. Each pen would be dedicated to deliver a particular medication, e.g., such as a short acting insulin (e.g., Humalog®, NovoLog®, Apidra®, or other) or long acting insulin (e.g., Lantus®, Levemir®, Toujeo®, or other). For example, the disclosed intelligent medicine administering system can be configured to allow having pens for more than one diabetes medication, which can include some additional features of the companion device 5. First, the software application resident on the companion device 5 can include a Total Daily Dose Calculation module, in which a total daily dose is determined to be the average sum of all insulin delivered (e.g., both long and short acting) in a day. This average may be calculated over different periods of time like week, month, quarter, etc. In addition, the software application resident on the companion device 5 can include drug confusion alerts that can be provided to the user via the display unit of the companion device 5. For example, with a drug confusion alert, the companion device 5 can alarm the patient if the patient injects a drug at the wrong time (e.g., because it indicates that there was confusion on which pen device the patient used). Also, for example, if the patient typically injects long acting insulin in the morning and delivers a dose in the afternoon, a mistake likely occurred. The typical delivery time could be set either explicitly (e.g., set a typical time and window for that delivery time) or experimentally where the average delivery time and typical window are analyzed to determine if a dose differs from the normal pattern. Drug confusion alerts can also be used in the hospital setting where an injection (or planned injection) can be cross checked with the Electronic Medical Record (EMR) or physician order to determine if the dose was correctly delivered, if there is a possible drug interaction, etc.

Another drug that can be used in the treatment of diabetes is glucagon. Glucagon raises the blood sugar. For example, if a patient's blood sugar starts to go low either because of too much insulin, too little food, too much exercise, or due to any of a variety of other factors, the patient may give himself/herself some glucagon to raise the blood sugar. Currently, Glucagon is typically delivered in a 1 mL rescue dose. However, it is anticipated that in the near future, microdosed glucagon can be delivered in only the volumes needed, and such microdosed glucagon vials will be developed. The disclosed intelligent medicine administration system is capable of tracking glucagon delivery. The tracking of glucagon can provide several advantages. First, there would be a record of the medication for health care providers. Currently there is no electronic record of glucagon deliveries. Second, any dosed glucagon should be considered in a dose calculator for future doses. The pen device 10 can be configured to store microdosed glucagon cartridges and detect, process, and/or transmit such dispensings with the companion device 5. For example, the disclosed intelligent medicine administering system can include one or more pen devices 10 configured to store and dispense the patient's diabetes medications from the medicine cartridge, e.g., insulins, and one or more pen devices 10 configured to store and dispense the patient's microdosed glucagon from the cartridge. The software application of the companion device 5 can include glucagon in dose calculations of the patient's proper next insulin dose and/or determine or set a glucagon dose, e.g., by considering a "Glucagon on Board" amount. This amount can be determined in the same way as insulin on board is currently determined using the software application. However, the action time of glucagon is much shorter. The dose calculator would include a "glucagon factor" or "Glucagon Sensitivity Factor" which can describe the patient's blood sugar response to Glucagon, e.g., in mg/dL/mL or mmol/L/mL or other specified units. This factor can be used both to determine a future rise in blood sugar due to recently injected glucagon as well as an amount of required glucagon prior to injection. By using the exemplary equation: Rise in blood glucose=Glucagon dose× Glucagon Factor; the calculator can determine the amount of glucagon required to raise the blood sugar a desired amount. This desired amount can be entered by the user or determined by the dose calculator based on excess "Insulin on Board".

Similarly, other drugs would benefit from the disclosed technology as well. For example, Follistim® is a drug used to treat infertility. In the case of Follistim, the typical dosing is a once or more a day regimen for several days. This regimen will begin several days following a woman's menstrual cycle. This dosing regimen is hard to remember. In this example case, a dose aid can be provided where the woman records her cycle. The aid then shows what days to take the drug. If the dose is given on those days, no alarm sounds. If the dose is not given by a particular time (e.g., perhaps user entered, or physician entered), then an alarm can sound to remind the user to take the dose. If a dose is given on an incorrect day, then an alarm is sounded to warn the user of this as well. Because infertility treatment is expensive, implementations of drug dose setting and delivery tracking by the disclosed technology can include using a data network (e.g., cellular, Wi Fi or other) to communicate the dosing history and especially dosing problems to the patient's treating physician (e.g., database at the treating physician's office) so that they may follow up with the patient if desired.

In another example, other drugs that can benefit from dose reminders of the disclosed technology include Lovenox®, Enbrel®, Humira®, and others. In addition, the software app of the companion device 5 may provide a symptom tracking feature for the patient to input and track symptoms that the drug is intended to alleviate so that there is a better record of symptoms for the physician to make drug choice and dosing decisions. Additionally, the symptom tracking feature can allow the patient to record side effects associated with use of the drug. In implementations for symptom tracking and/or side effect tracking, for example, the user interface of the software application can provide a menu of possible symptoms or side effects which makes tracking easier. For example, if headache is a common side effect, the menu might provide a slider for headache with limits including none and extreme so the user just moves the slider to the appropriate area and leaves it. Side effect and symptom information could be transmitted real time to the user's caregiver (e.g., user's doctor office), and/or can be stored for later review during an office visit or transmitted only if a specific threshold is reached. For example, the software application might ask if a user has experienced shortness of breath and any answer of "yes" or on a sliding scale "moderate" or more might be automatically transmitted to the physician.

Because multiple drugs may be used with the product, multiple detection features for ensuring that the correct drug is loaded can be included in the pen device 10 and/or companion device 5. For example, there may be several drugs that are desired to use and in this case knowing which drug is loaded is useful. Drug cartridges are provided with unique codes on the cartridges such as bar codes. The companion device 5 can include a camera to capture an image of the bar code on a medicine cartridge that can be processed by the data processing unit to identify the type of drug being loaded. For example, the processed data associated with the image captured by the camera of the coded cartridge can be used by the processing unit to identify the actual drug being loaded and generate an alarm if an incorrect or wrong drug is being loaded (e.g., based on data provided by the patient using a user setting of correct drugs), or confirm that the correct drug is being loaded. In the case of use of multiple drugs, the software application can be configured to provide features and the interface associated with a particular drug loaded, e.g., in accordance with the correct drugs listed for the specific patient. For example, different dose calculation parameters, different tracking parameters, or metrics can be stored, and/or identification of each dose tracked as having come from that drug. In an illustrative example, if the user uses two types of insulin, in which one type has an action time of 3 hours and the other type has an action time of 5 hours, then the device 10 can detect which drug the user is loading and provide that parameter to the dose calculator algorithm automatically.

Dose Distinguisher

Patients may need to dispense a prime or priming dose prior to injecting the therapy or therapeutic dose. For example, in some use cases, the patient will replace their needle and deliver a prime dose intended to clear the new needle of air. In some cases, for example, a prime dose will be delivered even though the needle was not replaced. In some cases, for example, a prime dose will not be delivered even though the needle was replaced. It is necessary to be able to determine which doses are the prime doses and which are therapeutic doses, in which data associated with the determination of the dose type should be included in the dose calculation (e.g., "Insulin on Board" calculation) and the therapy analytics. Typically, when a prime dose is delivered, it is followed by a therapy dose. In some implementations of the intelligent medicine administering system, for example, the software application of the companion device 5 can include a dose distinguisher or identification module to process dose dispensing data and determine and distinguish between a prime dose and a therapy dose that was dispensed from the pen device 10. In some implementations of the intelligent medicine administering system, for example, the data processing unit on the pen device 10 can include the dose distinguisher module to process dose dispensing data and determine and distinguish between a prime dose and a therapy dose that was dispensed from the pen device 10.

In some embodiments, the dose distinguisher module is configured to implement a dose classification method to group data associated with dispensed medicine doses and classify the dispensed doses in the group as either a prime dose or an injected (e.g., therapy) dose; such that, for any group of doses happening in close temporal proximity, only the last dose is recorded as a therapeutic dose. The close temporal proximity is a predetermined temporal threshold value, e.g., which can be defined as 10 seconds, 30 seconds, 1 minute, 2 minutes, 5 minutes, or 10 minutes or other.

Identifying doses as prime is very important in patients with low insulin requirements. For example, in a child, a typical prime dose may be 2 units while a typical therapy dose may be 0.5 or 1 units. In this case, if a user were to include all dispensed insulin in the tracking (rather than only the therapeutic insulin), then the therapy tracking would be wrong as would any insulin on board calculations or future dose recommendations. This is one example showing that prime doses cannot be distinguished based solely on size. In the example given above, the therapy dose is much smaller than the prime dose, but with a fully grown adult or a type 2 patient, the therapy dose may be much larger than the prime.

In some cases, for example, a user may prime their device and not deliver a therapeutic dose. To prevent the dose distinguisher module from improperly identifying the dose as a therapeutic dose, in such cases, the system can include an additional mechanism that may be utilized to quickly identify the dose as either "prime" or "therapeutic". In one example of this additional dose identification mechanism, a user verification input can be included in the software application of the companion device 5 to allow the patient to identify that the recorded doses were one of the prime or therapy doses, which would then allow for such doses to be included in any therapy analytics and insulin on board calculation, as appropriate. This user verification input mechanism can include a radio button, a toggle switch, and/or graphic of the user interface allowing tapping on the dose, slider, or other mechanism.

In some embodiments, for example, the dose distinguisher module can be configured to include one or more additional processes or exceptions to the exemplary dose classification method to group and classify the last dose of a group of doses happening in close temporal proximity as a therapeutic dose. In an example, the dose classification method can be implemented such that following a cartridge replacement, if there is only a single dose, it would be designated a prime dose and not a therapy dose. In another example, the dose classification method can be implemented such that when a first dose (or intermediate dose) is larger than a predetermined dose quantity threshold, that dose is considered therapy. For example, any dose determined to be larger than 2, 5, 10 units or other size could be considered therapy regardless of their position in the dose sequence.

The dose distinguisher module of the disclosed systems to determine prime doses from therapeutic doses can include a separate dosing knob on the pen device 10 for prime dosing. The exemplary separate dosing knob can be structured to actuate the dose jackscrew, but not the dose encoder (as described later in this patent document). In these embodiments, for example, when the user rotates the separate dose knob, the medicine is injected but the encoder does not count the dose.

The dose distinguisher module of the disclosed technology to determine prime doses from therapeutic doses may include additional or alternative methods for dose distinguishing. In one example, a method to determine if a dispensed dose is prime or not includes sensing if the pen device 10 is in contact with the body at the time of injection. This can be done in any of several ways. In one non-limiting example, the pen device 10 can include a pressure sensor coupled to the needle assembly or tip or end of the body of the pen device 10 to determine if a force has been applied at the needle assembly or tip of the device (as when injecting). In one non-limiting example, the pen device 10 can include a capacitive sensor fitted near the end of the device which would sense proximity to the body. In either of these exemplary cases, sensing pressure or proximity would result in the dose being considered therapeutic and not prime.

The dose classification method to determine prime doses versus therapy doses can include detecting the speed of doses being delivered. For example, it is possible that prime doses are delivered at a faster rate than non-prime doses. The encoder mechanism of the pen device 10 can be configured to record the speed of the dose, e.g., in which the speed data is transferred to the companion device 5 for processing. The speed may then be compared to a predetermined dose rate threshold to determine if the dose is prime or not. For example, the encoder mechanism can detect the speed, where the threshold will depend on the gear ratio, and the encoder counts per revolution and/or other factors. It may be determined that doses resulting in average dose speeds over a pulse per second threshold are prime doses. This dose rate threshold could be determined by asking users to deliver a series of both prime and therapy doses and comparing the average dose speed of each. If there is little overlap in the dose speed ranges of each type of dose then dose speed is a good indicator of type of dose. In some implementations, for example, the dose distinguisher module can utilize the detected dose speed in addition to the dose dispensing groupings within the predetermined amount of time proximity to identify the therapy dose from a prime dose. In some implementations, for example, the dose distinguisher module can utilize the detected dose speed without consideration of the sequence of doses in a dose dispensing grouping.

In some implementations, the dose classification method to determine prime doses versus therapy doses can involve the pen device 10 including a shroud assembly around all or part of the needle of the needle assembly and a sensor in the shroud assembly. In implementations, when the needle is injected into a patient, the shroud would contact the skin and slide back, triggering the sensor to detect and indicate an actual therapy dose. If the shroud does not move back, it would indicate the pen was being held in the air and the dose would be considered a prime. Alternatively, instead of the shroud, the sensor can be structured in an assembly including a small button or lever that contacts the skin and functions similarly.

In some implementations, the dose classification method to determine prime doses versus therapy doses can involve the pen device 10 including an internal accelerometer, gyroscope, or other rate sensor to detect movement data of the pen device 10, which is transferred to the companion device 5 to analyze the movement data. For example, if the pen 10 senses an inward motion before the dose is dispensed and an outward motion after the dose is dispensed, the companion device 5 would indicate that the pen 10 had been injected into a patient and thereby identify the dispensed dose as a therapy dose; whereas if these motions were absent, it would indicate that the pen 10 had been held in the air.

In some embodiments of the dose distinguishing module, for example, the module can include a 'voting' method to determine if a dose is a prime dose. In an illustrative example of the voting method, the dose distinguishing module can implement multiple embodiments of the dose classification method in parallel for a particular dosing sequence, e.g., such as the exemplary dose grouping process (e.g., identifying the last dispensed dose in a sequence of doses dispensed in a predetermined time proximity as the therapy dose), the exemplary dose speed detection process, the exemplary movement data detection process, etc. If after a particular dosing or dosing sequence, a certain majority of the exemplary methods for dose distinguishing indicated that the dispensed dose is a prime dose, and a minority method indicated it is not, then the voting method would determine that in this case the dose would be identified as a prime dose.

Interaction with External Devices

In some embodiments, for example, the pen device 10 or the companion device 5 can receive health related information such as blood glucose information from an external device (e.g., such as a blood glucose meter or continuous glucose monitor) for use in the dosing calculations. This information could be manually entered, downloaded manually or automatically from a central health information repository, e.g., such as Apple "Healthkit" or Google "Fit", or received wirelessly onto the companion device 5. In addition to being used in the dosing calculations, for example, the most recent health related data (e.g., blood glucose information) could be displayed on the companion device 5, or the pen device 10 in certain embodiments. If recent blood glucose information was available from one of these sources, it could automatically be entered into the dose calculation device. In these examples, 'recent' for the purposes of blood glucose measurement can mean any time period in a range of 0 to 20 minutes old.

In some embodiments, for example, the pen device 10 or the companion device 5 can receive health related information such as carbohydrate consumption information that may be entered manually by the user, or received from either a secondary application on the companion device 5 or a central health repository, e.g., such as Apple "Healthkit" or Google "Fit", received wirelessly onto the companion device 5. In addition to being used in the dosing calculations, the most recent carbohydrate information can, in some implementations, be displayed on the companion device 5, or the pen device 10 in certain embodiments. In some implementations, if recent carbohydrate information was available from one of these sources, it would automatically be entered into the dose calculation device. In these examples, 'recent' can mean any time period in a range of 0 to 20 minutes old.

In various embodiments, at the time that the dose is to be calculated, the companion device 5 can verify that it has the most up to date dose information by communicating with the pen device 10. In some implementations, for example, if communication with the pen is unavailable, then the automated dose calculation features would not function or would only function after a user acknowledged a warning. The system can include such a safety mechanism to ensure that additional medicament (e.g., insulin) has not been given that has not been included in the dose calculation. In some embodiments, for example, other mechanisms can be included to know if the pen device 10 had recently communicated with the companion device 5, e.g., such as the dose calculation being shown in different colors (e.g., red for no recent communication, and green for recent communication), the "Insulin on Board" (IOB) feature being shown in different colors (e.g., red for no recent communication, and green for recent communication), and/or a communication icon being present or not or changing color to indicate current communication or not. In some embodiments, for example, a mechanism for communication of information regarding doses and IOB could be through haptic feedback where a single vibration or series of vibrations over time (e.g., such as via a vibration motor) could indicate the status to the user. In these examples, 'recent' can mean any time period in a range of 0 seconds to 2 hours.

Communication Checking

The system includes communication checking between the pen device 10 and the companion device 5, which can provide protections from inappropriate dosing by the patient. For example, in some embodiments, the software application of the companion device 5 can prompt or ask the user if they would like to enter doses manually. If the user answers "yes", then the dose calculator would be allowed to function although a message to the user would warn them that dose recommendations may be dangerous if they do not track all of their doses. If the user answers "no", then the dose calculator will remain disabled until communication with a pen is re-established.

Pairing of Dosing Events Between the Pen and the Companion Device

In some embodiments, once the dose calculator has been used and a dose has been delivered, these events can be "paired" as having been related, e.g., via the software application on the companion device 5. Because the dose could be delivered manually by the pen device 10 (and not commanded by the companion device 5), it may be necessary or desired to determine if the dose calculator was used to determine the size of this specific dose. The time between events may be used to "pair" these events. A window of time that the two events happen within could be used. For example, if a dose happens within ±1, 2, 5, or 10 minutes of a dose calculator use, then those events could be paired as related.

Alerts and Safety Features

In some implementations, for example, the companion device 5 transmits the calculated dose to the pen device 10 for delivery. In some implementations, for example, the companion device 5 transmits the recommended dose to the pen device 10 which then provides a mechanical lock-out which prevents the user from delivering more medicament than was calculated as a recommended dose. In some implementations, for example, the software application of the companion device 5 provides a process to override the dose lock out feature on to give a larger dose if desired.

In some embodiments, for example, the companion device 5 and/or the pen device 10 is provided with a method to warn the user if a bolus has been recently taken. This is a safeguard against accidentally double dosing for a meal or taking long acting insulin twice in a day. This alarm could be active if a second dose is initiated within a predefined period of time after the previous dose. If the alarm became active, it could be signaled to the user through an audio, visual, and/or tactile (vibratory) method. In some embodiments, for example, the companion device 5 and/or the pen device 10 can warn the user of a missed dose. A missed dose can be identified if a dose has not been given within a certain period of time after a specific time of day or after an average time of bolus. For example, with long acting insulins (e.g., Lantus®) the injections are usually given once a day at a specific time of day. The companion device 5 and/or the pen device 10 could average the time of the injections given on a daily basis and then give a missed dose alarm if no dose is sensed within predetermined or user settable amount of time after that average time, e.g., 2 hours.

In some embodiments, the companion device 5 and/or the pen device 10 can provide an alert to warn the user of excessive insulin on board (IOB). For example, if the total IOB exceeds a threshold which is user settable to related to the max dose in some way, then the system can generate an alarm to inform the patient that the patient may have potentially overdosed. This overdose may be caused by several smaller doses adding to more than the user intends, which is referred to as stacking.

In some embodiments, the companion device 5 and/or the pen device 10 can provide an overdose alarm. This alarm would be triggered if the dose injection history and the bolus update when injected predict a potential for harm due to excess medicament in the patient. For example, the alarm could be triggered of successive doses of similar size are detected because that is an indicator of double dosing. The system could provide the alarm if a dose much larger than is recommended is taken. For example, a much larger dose could be either a ratio (e.g., more than double) or a fixed amount greater (e.g., more than 2 units greater, or a combination where fixed differences are used at the low end (perhaps under 5 units or so) and ratios are used above that.

The disclosed systems include a maximum dose setting feature. Typically, the user (patient or health care provider) sets a maximum dose in the settings of the software application resident on the companion device 5 and the user is either prevented from delivery a dose above that or warned before they do. Alternatively, in some examples, a dynamic maximum dose alarm could be used by the system. This feature would determine a maximum dose based on the patient's history over the last period of time, e.g., perhaps week, month, quarter or other time period. By looking at the dose history over that time period, a maximum dose level can be set multiple ways. In one example, the maximum dose level can be set by taking the highest dose in the period, e.g., the average of the 3, 5, 10 or more highest doses, the average dose plus some number of standard deviations of dose, the average highest dose time some factor (e.g., 1.1, 1.2 etc.) or another method or methods.

With the above exemplary features, the companion device 5 allows the dose history as well as any entered or received dose parametric data to be reviewed by a physician or the patient or other interested party, e.g., such as an insurance company. This review could be on the display screen of the companion device 5, for example, or also prepared in a report for transmission to either a computer, e.g., directly or via the cloud. This transmission could occur wirelessly or through a wired interface. Wireless transmission would include uploading to cloud based servers, email to a selected address, fax to a selected fax number or even being sent directly to a printer possibly through a service such as Airprint. The report could be formatted several ways including but not limited to .PDF, .CSV or .JSON file formats.

In various embodiments for hospital, clinical, or physician care use, for example, the pen device 10 and/or the companion device 5 can log and verify doses to a patient. This can be used, for example, to cross check a physician order to a specific patient. The order could be entered electronically by the physician, and the companion device 5's software application would use a method to verify the patient identity (e.g., barcode scanner, facial recognition, RFID, or other electronic means), the pen could then be unlocked for a given period of time to allow the medicament to be injected. If the dose was not correctly administered (the wrong amount of medicament doses) then, in some implementations, an alarm would be presented on the application and sent to the physician.

As discussed above, the companion device 5 to which and/or from which information can be transmitted can include, for example, a stand-alone mobile electronic device, or a multi-application device such as a smartphone, a smart watch, a tablet, a laptop, or a non-mobile electronic device such as a desktop, television, or devices such as a Qualcomm 2Net hub or could also be the cloud (internet-based servers). In some embodiments, for example, the patient wears a wearable companion device that can provide pertinent information such as insulin on board, blood glucose, or a display of continuous glucose monitoring. This wearable device can be a device dedicated to the pen device 10, or it can be a multi-application device such as a smartwatch or Fitbit-type device, or other. In some implementations, the wearable device may be the only companion device associated with the pen device, and in other implementations, the wearable device is a second companion device that provides a more limited interaction with the user, e.g., providing blood glucose data and indicating dose time. The wearable companion device can be designed to attach to the user in any configuration, for example on the wrist as a watch-type device, as a patch, or as a clip-on to clothing. The transmission can occur through any wireless protocol, for example Bluetooth, Bluetooth low energy, WiFi, ZigBee or any other appropriate wireless protocol.

In addition to the dose information uploaded from the pen device 10, additional dose information could be entered into the companion device 5 manually. This can assist in facilitating dose tracking from devices other than the pen device 10, or when the pen device 10 is not communicating (e.g., dead battery, broken processor) or when the pen device 10 is out of range. In the exemplary case where the companion device 5 is in the cloud, a web based portal could be provided to allow entry of information.

This dose information can be displayed to the patient, physician or other interested party. This display can be on the display screen of the companion device 5 or through generation and transmission of a report. The transmission of the report could be email, or direct transfer to the cloud, or direct printing or any other method of communicating the information from the companion device 5 to a method of display to a person. In order to transmit the information, a contact list on the companion device 5 may be used to select a person, address or other destination for the transmitted information to be sent to.

In some implementations, for example, the information that the patient or health care provider can view, or transmit, may include any pertinent data, e.g., such as typical therapy analytics. In addition, it may contain new metrics such as insulin modal day. This graph shows average blood glucose data for each hour of the day. In some embodiments, this is determined by averaging and reporting all blood glucose measurements taken in the report period between two time periods (e.g., typically one hour apart). For insulin the total amount of insulin given within the report period (e.g., typically 7 days to 90 days) between the two times are added and divided by the number of days in the period. This produces a graph of the average insulin delivered through each hour of the day. By adding the measurement for each hour of the day the result would be the total average insulin delivered each day.

In some implementations, for example, another metric that is displayed on the screen or report is dose histogram. This display may be configured as a typical histogram showing how many doses of each size were delivered. Typically, for example, this histogram would be divided into multiple buckets (e.g., 10 buckets but more or less would be possible). The graph allows the patient or health care provider to get a visual indication of the size of the doses taken in total. This indication can help determine if the patient is on fixed dose therapy, correctly carbohydrate counting, etc. and can guide the health care team to help the patient in the correct way.

Dose Recommendation

The pen device 10 and companion device 5 may also be used to generate dose recommendations for the patient, e.g., based at least in part on the produced a dose output generated by the dose calculator. In diabetes specifically, for example, the dose the patient is going to take is commonly based on carbohydrates to be eaten, current blood sugar, and current insulin on board the pen device 10. Any or all of this information could be entered into the companion device 5 such that the companion device 5 can generate a dose recommendation that the user could then take (i.e., inject) using the pen device 10. In some implementations, for example, the dose recommendation would be transmitted to the pen device 10 for the user to inject, and in some examples may display on a display screen of the pen 10. In some implementations, for example, the patient must manually receive the dose recommendation from the companion device 5 (e.g., view the dose recommendation on a display screen of the companion device 5) and enter it into the pen (e.g., set the recommended dose using the dose setting mechanism of the pen device 10).

Because dose recommendations are based, in part, on current insulin on board, if the companion device 5 is unaware of recent doses, then the recommendation may not be correct or appropriate. For that reason, in some implementations, the dose calculator will not offer or provide a dose recommendation unless communications with the pen device 10 have recently occurred. This can ensure that the insulin on board (IOB) information is up to date. Once the dose recommendation has been generated, for example, it can either be entered into the pen device 10 and dosed, or it could be viewed remotely by a third party. The dose could then be remotely approved by the third party. The approval could constitute a message of approval, allowing the companion device 5 to display the dose suggestion, allowing the dose suggestion to be transmitted to the pen device 10 or unlocking the pen device 10 to allow injection of the dose.

Temperature Sensor

In some embodiments, for example, the pen device 10 includes a temperature sensor to detect temperature of or near medicine cartridge, in which the detected temperature data is reported to the companion device 5 to record current and past temperatures associated with the pen device 10. For example, the temperature data can be used by the companion device 5 to determine if the medicament has exceeded a critical temperature threshold. If a temperature limit is exceed, the companion device 5 can produce an alarm (e.g., providing a visual, haptic, or sound) to alert the user. In some implementations, for example, a temperature time limit can be used in the determination of the status of the medicament. For example, the temperature time limit metric is an integration of the temperature time curve where larger numbers indicate greater exposure to temperature extremes. This temperature information can also be used to modify dose calculations based on known temperature effects to the medicament.

Medicine Cartridge Retraction Detection

In some embodiments, for example, the pen device 10 can be configured to sense the replacement of a cartridge by detecting the retraction of the lead screw. For example, when the medicine cartridge is replaced by another medicine cartridge, the lead screw will be retracted which would cause the encoder to spin (and record movement). If the encoder were to indicate travel in an opposing direction (e.g., negative direction or away from dose) and/or of an indicative value of greater than a predetermined threshold number of units (e.g., 1, 5, 10 or other, as in the case of insulin) or other metric with other drug, then this data can be processed by the system (e.g., the data processing unit of the companion device 5 or within the pen 10 itself) to determine that the medicine cartridge has been replaced. In the case of a replaced cartridge, for example, active temperature alerts would be cleared, e.g., because any drug like insulin that was suspect has now been replaced. Also, for example, any modifications to the dose calculator algorithm based on known temperature effects of the insulin could also be cleared.

Bonding/Pairing of the Pen and the Companion Device

In some implementations of the disclosed intelligent medicine administering system, the pen device 10 can be 'bonded' or 'paired' to the companion device 5 and 'unbonded' or 'unpaired' to the companion device 5 based on the following security communication methods. For example, the bonding of a particular pen device belonging to the user to a particular companion device of the user (e.g., the user's smartphone device, tablet, etc.) may need to be reset or cleared so that that the particular pen may be bonded to a new companion device of the user or other (e.g., such as a new smartphone, tablet, etc. of the user). The bonding security feature can include a security code that the user enters on the companion device 5 via the user interface of the software application after the pen device 10 is detected by the companion device 10 as a pen device to be bonded. The unbonding security feature can include a program stored in the memory of the pen device 10 and/or in the cloud for providing to a new companion device, in which the program is created by the user operating a particular pattern of detectable implementation events performed on the pen device 10. For example, the program can unlock the pen-companion device bonding between the pen device 10 and the initial companion device 5 (e.g., which may have been lost, damaged, or replaced by the user) when the user implements the pattern, e.g., and therefore allow the pen device 10 to be bonded to another companion device of the user. For example, the program could include a pattern of dosing events (e.g., without a cartridge to avoid wasting medicine), e.g., such as 2-5-2-7: dispensing of 2 (empty) units, 5 (empty) units, 2 (empty) units, and then 7 (empty) units, or any other pattern. For example, the program could include a pattern of setting events, e.g., such as by turning the jack screw in and out in a certain pattern (e.g., turn in more than two units, turn out more than two units, etc.), which could include repeating this pattern at least 1, 2 or 3 or more times all within a fixed period of time (e.g., 1, 2, 5 or more seconds). Implementation of the user-set pattern would enable the pen device 10 to be set back in a mode where it may be bonded or paired to a new companion device 5.

In some implementations, for example, the companion device 5 can include hints or reminders of the user-set program in cases where the user forgets the pattern he/she set. Such information can be encrypted and stored in memory on the companion device 5, or in the cloud in an account, or sent to the user via electronic communication (e.g., such as a text, email, etc.). In initial set-up of the pattern, the companion device can display a summary of the pattern for approval for the user, e.g., to ensure that the user is aware of the pattern in the program capable of unbonding the pen-companion bonding relationship.

Figure 3A:
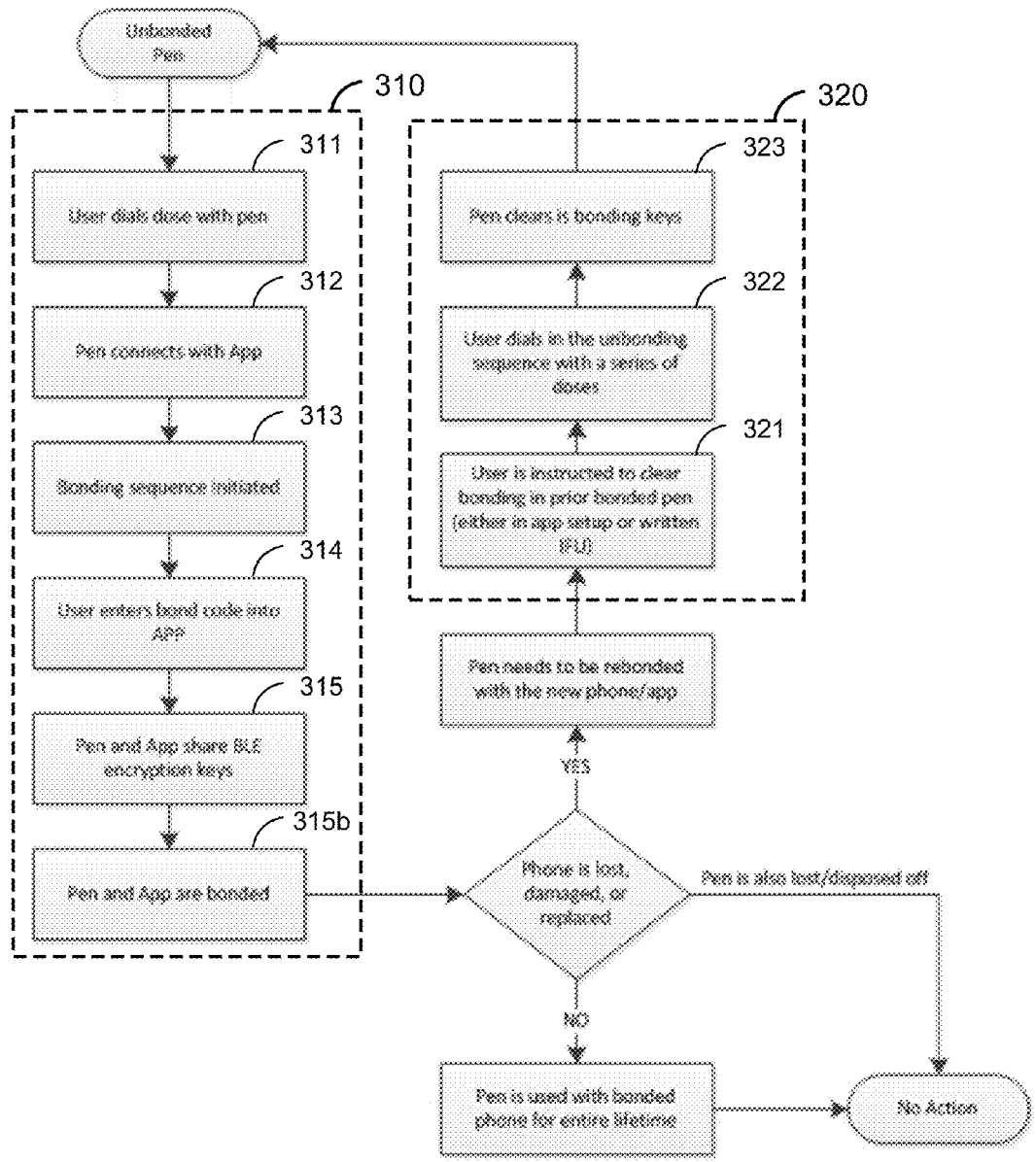
FIG. 3A shows a flow chart diagram of an exemplary method of bonding and unbonding a pen device from a companion device.

FIG. 3A shows a flow chart diagram of an exemplary method of initial bonding of the user's pen device 10 to the user's initial companion device 5 and unbonding of the pen device 10 from the initial companion device 5 to allow for subsequent bonding of the pen device 10 to the user's new or other companion device 5. A method 310 can be implemented by the devices to bond the pen device 10 to the initial companion device 5. The method 310 includes a process 311 for the user to perform a dose setting and/or dispensing operation (e.g., dial a dose) with the pen device 10. The method 310 includes a process 312 for the initial companion device 5 to communicatively connect with the pen device 10. The method 310 includes a process 313 for the initial companion device 5 to initiate a device bonding sequence to bond the pen device 10 to the companion device 5. The method 310 includes a process 314 to prompt the user, e.g., via the display of the initial companion device 5, to enter a bond code (e.g., such as a default code in the instructions of the pen device 10, or a code sent independently to the user for entry) on the user interface of the software application of the initial companion device 5. In some implementations, for example, the bond code can include a numeric, alphabetic, symbolic, or other text based code. The method 310 includes a process 315 to provide encryption keys (e.g., BLE encryption keys using a Bluetooth communication protocol) to the pen device 10 and the software application on the initial companion device 5, and thereby bonds the devices. The method 310 includes a process to 315b to conclude the bonding method 310.

The pen device 10 may remain bonded to the initial companion device 5 indefinitely, e.g., for the entire lifetime of the devices. If the pen device 10 is lost or disposed of, for example, then the user may replace the pen device 10 with a new pen device 10, in which the new pen device 10 can be bonded to the initial companion device 5 by implementation of the method 310. If the initial companion device 5 is no longer accessible to the user, e.g., due to being lost, stolen, damaged, or replaced, the pen device 10 can undergo a method 320 to unbond the pen device 10 from the inaccessible initial companion device 5.

The method 320 includes a process 321 to initiate prompt the user, e.g., via a display of the new/other companion device 5, to clear the bonding of the pen device 10 from the initial companion device 5. For example, the process 321 can include providing instructions, e.g., on the display of the new/other companion device 5, for the user to perform two or more dispensing operations of the injection pen device in a predetermined time frame. In some implementations of the process 321, for example, the process 321 includes initiating, at the new/other companion device 5, a count of the predetermined time frame, e.g., which may be displayed to the user. As the user performs the two or more dispensing operations, e.g., dialing and dispensing two or more (empty) doses using the pen device 10, a process 322 of the method 320 is implemented to receive, as the new/other companion device 5, such pattern data associated with the operations of the pen device 10 performed by the user over the predetermined time frame. The method includes a process 323, at the pen device 10, to clear the bond code and associated encryption keys associated with the initial companion device 5, and thereby unbonds the pen device from the initial companion device 5. The pen device 10 and the new/other companion device 5 can then implement the method 310 to bond the devices.

For example, in some implementations of the method 320 of unbonding an injection pen device from a bonded mobile communication device, the method 320 can include displaying instructions to a user of the injection pen device that has been communicatively bonded to the initial companion device 5 (e.g., a first mobile communication device), via a display screen of the new/other companion device (e.g., second mobile communication device), to perform two or more operations of the injection pen device in a predetermined time frame; initiating, at the second mobile communication device, a count of the predetermined time frame; receiving, at the second mobile communication device, pattern data associated with the operations of the injection pen device performed by the user over the predetermined time frame; and transmitting, from the second mobile communication device to the injection pen device, a clearing code to cause the injection pen device to clear encryption keys associated with first mobile communication device. In some implementations, for example, the method 320 can include storing the pattern data in a database including a user account of the user. In some implementations, for example, the second mobile communication device can then initiate a bonding sequence to communicatively bond the second mobile communication device with the injection pen device, e.g., to implement the method 310. For example, in some implementations of the method 310, the method can include prompting the user, at the display screen of the second mobile communication device, to enter a bond code into the second mobile communication device; receiving, at the second mobile communication device, the user-entered bond code; and providing, at the second mobile communication device, encryption keys to the injection pen device and the second mobile communication device. For example, the bond code includes a text based code including numeric text, alphabetic text, symbolic text, or a combination thereof.

Figure 3B:
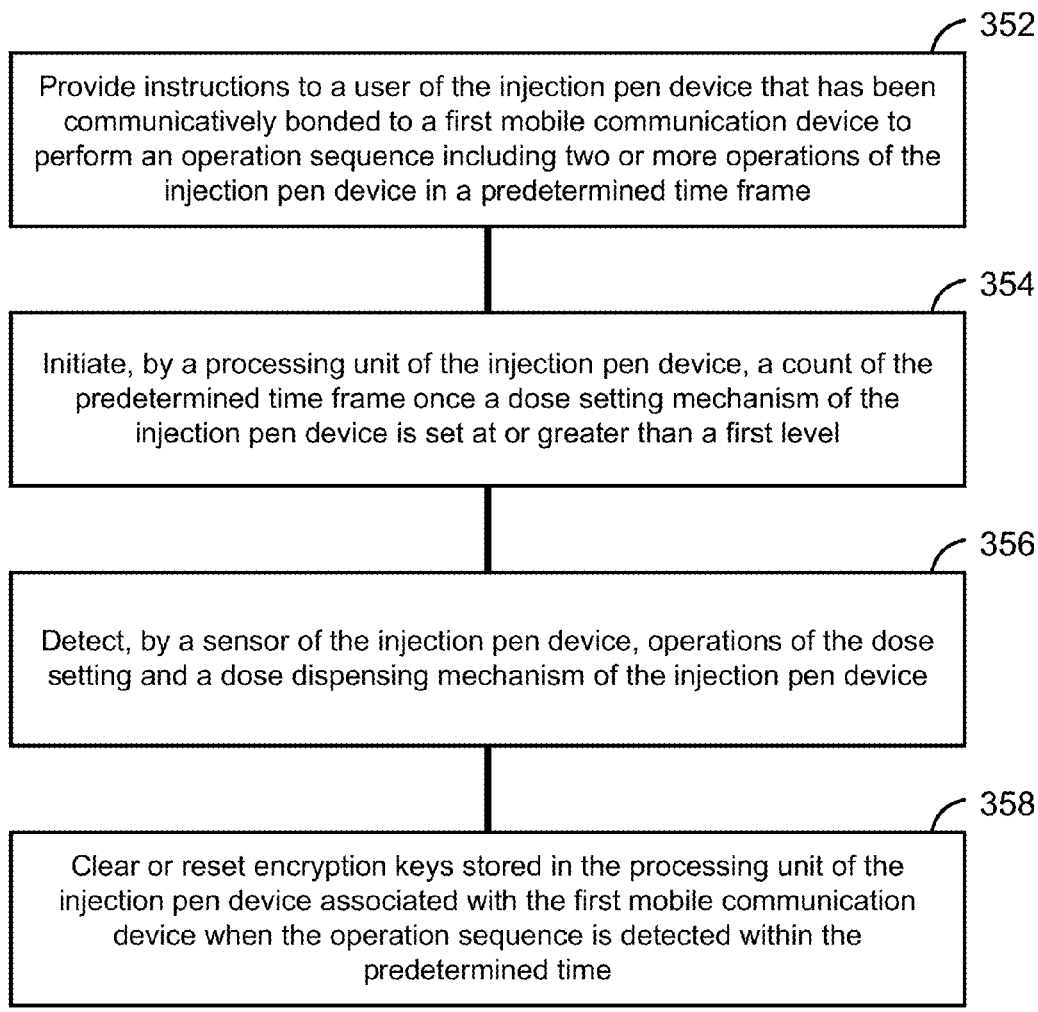
FIG. 3B shows a diagram of an exemplary method of unbonding a pen device from a companion device.

FIG. 3B shows a diagram of an exemplary method of unbonding a pen device from a companion device. The method includes a process 352 to provide instructions to a user of the injection pen device that has been communicatively bonded to a first mobile communication device to perform an operation sequence including two or more operations of the injection pen device in a predetermined time frame. The method includes a process 354 to initiate, e.g., by a processing unit of the injection pen device, a count of the predetermined time frame once a dose setting mechanism of the injection pen device is set at or greater than a first level. The method includes a process 356 to detect, e.g., by a sensor of the injection pen device, operations of the dose setting and a dose dispensing mechanism of the injection pen device. The method includes a process 358 to clear encryption keys stored in the processing unit of the injection pen device associated with the first mobile communication device when the operation sequence is detected within the predetermined time.

Implementations of the method shown in FIG. 3B can optionally include the following exemplary features. For example, the instructions can include (i) operating a dose setting mechanism of the injection pen device to the first level or greater than the first level, (ii) operating the dose setting mechanism to a second level less than the first level, (iii) operating the dose setting mechanism to a third level greater than the second level, (iv) operating the dose setting mechanism to a fourth level less than the third level, and (v) operating a dose dispensing mechanism of the injection pen. Similarly, for example, the instructions can include (i) operating a dose setting mechanism of the injection pen device to the first level or less than the first level, (ii) operating the dose setting mechanism to a second level greater than the first level, (iii) operating the dose setting mechanism to a third level less than the second level, (iv) operating the dose setting mechanism to a fourth level greater than the third level, and (v) operating a dose dispensing mechanism of the injection pen. In some implementations of the method, for example, the process to provide the instructions can include displaying the instructions to the user on a display screen of a second mobile communication device to perform the two or more operations of the injection pen device. In some implementations of the method, for example, the method can further include a process to bond the injection pen device to the second mobile device by the following: initiating, by a second mobile communication device, a bonding sequence to communicatively bond the second mobile communication device with the injection pen device; prompting the user, at the display screen of the second mobile communication device, to enter a bond code into the second mobile communication device; receiving, at the second mobile communication device, the user-entered bond code; and providing, at the second mobile communication device, encryption keys to the injection pen device and the second mobile communication device.

Find My Pen

In some implementations, for example, the pen device 10 and companion device 5 may be in communication at various intervals from many times a second to once every several minutes or several hours. In instances where the companion device 5 includes a GPS system, the location of the companion device 5 can be determined, and therefore the pen can be known at each communication. For example, if the location of each communication or the last communication were logged and then the communication ceased, the system would know approximately where communication ceased. This can be extremely helpful in situations where the user loses his/her pen by leaving it behind somewhere, for example. The software application of the companion device 5 can then provide GPS coordinates, or a location on a map, or directions, or other information showing the user where he/she had left the pen device 10.

Exemplary User Interface and User Features

Figure 2C:
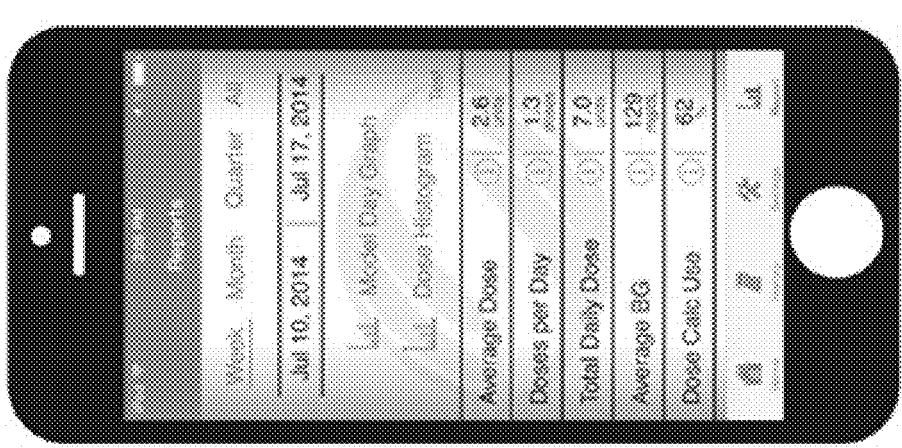
FIGS. 2A-2F show display screens of an exemplary user interface of a software application resident on the companion device of the disclosed intelligent medicine administering system.
Figure 2B:
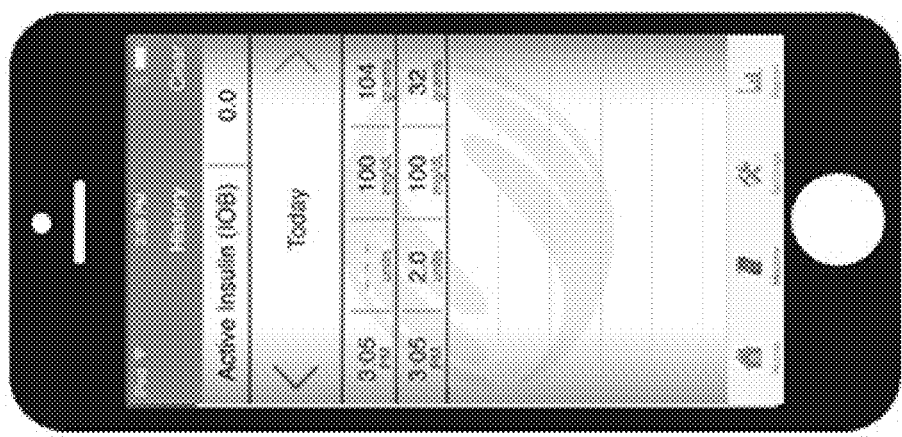
Figure 2A:
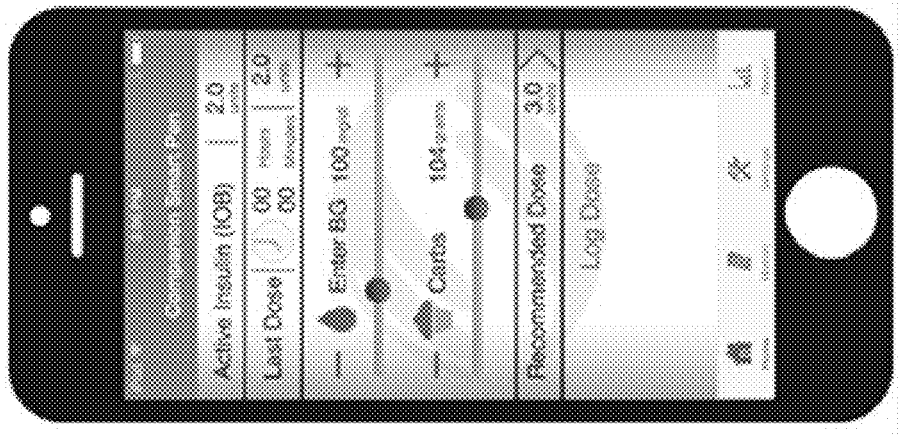

FIGS. 2A-2F show display screens of an exemplary user interface of a software application resident on the companion device of the disclosed intelligent medicine administering system. FIG. 2A shows an example of a user interface display for the exemplary dose calculator. For example, the exemplary dose calculator user interface can include information about the medicine loaded in the pen device 10 (e.g., active insulin) and/or dose information (e.g., including the time of the last dose, amount of the last dose, etc.). The exemplary dose calculator user interface can include an interactive region of the display that allows the patient to enter data about their recent analyte levels (e.g., blood glucose levels), carbohydrates intake, calories intake, or other food data intake or activity data. The exemplary dose calculator user interface can include a recommended dose (e.g., a certain amount of the medicine in the pen device 10) displayed on the screen based on the processed data, e.g., including the dose data received from the pen device 10 and the inputted data from the patient in the interactive region. In some implementations, for example, the exemplary dose calculator user interface can include an interactive button to log the dose to allow the patient to manually log a dose. For example, the log button feature could be used to manually log a dose in situations where the pen device 10 was not used. This could be that the patient has chosen to take a dose from another mechanism, e.g., such as a syringe, or that the battery of the pen device 10 has depleted and doses are no longer being logged.

FIG. 2B shows an example of a user interface display for an exemplary dose history record, which allows the patient to review their dose dispensing history for a particular medicine. For example, the exemplary dose history user interface can include information about the recent doses logged over a certain period of time, e.g., such as "today", or over selected days, weeks, or other time frame.

FIG. 2C shows an example of a user interface display for an exemplary therapy report, which can be available to patients and made available to healthcare providers. For example, the exemplary therapy report can allow healthcare providers to review administered therapies and make suggestions accordingly. The exemplary therapy report user interface can include an text and graphics presenting information on average doses of a particular medicine over a user-selected time period, doses per day, total daily doses, average analyte levels of the patient, dose calculator usage, the amount the average dose differs from the average recommended dose and other data.

Figure 2F:
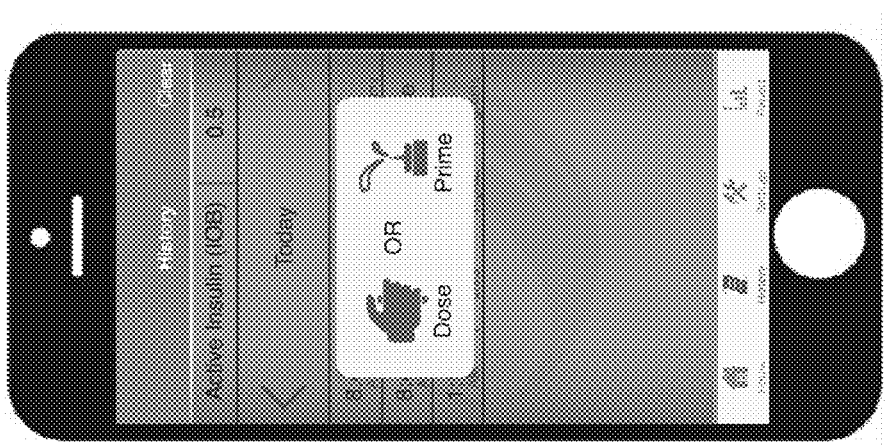
Figure 2E:
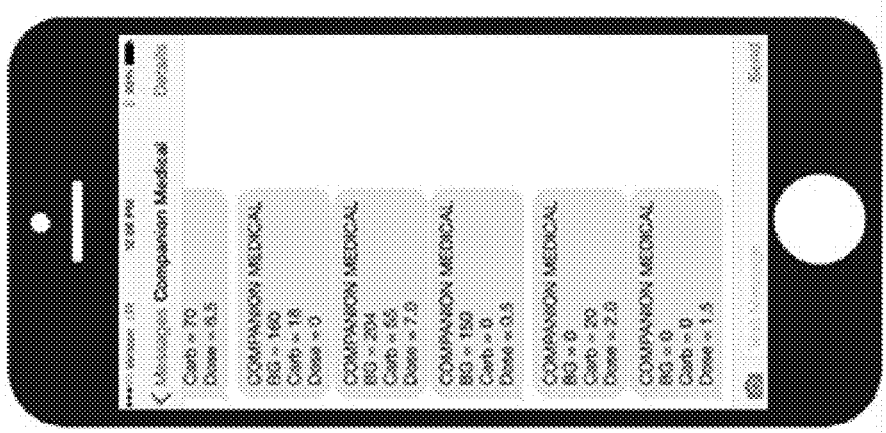
Figure 2D:
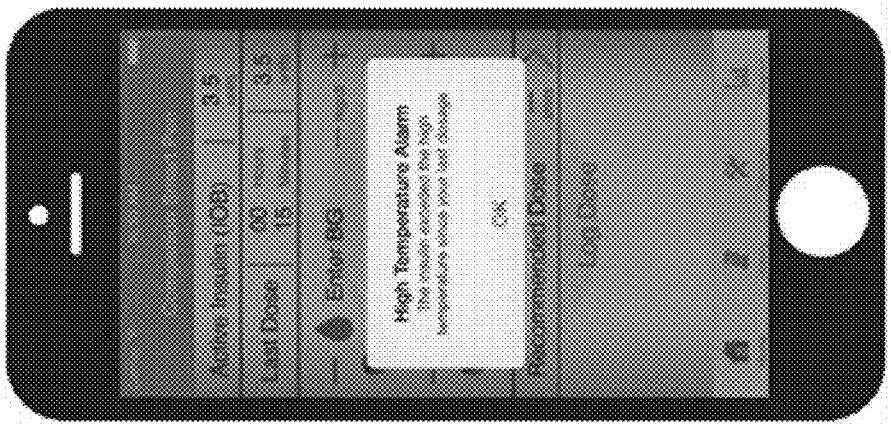

FIG. 2D shows an example of a user interface display for exemplary alerts. For example, the exemplary temperature alerts provides the users with urgent and/or actionable information regarding monitored parameters of the pen device 10 and/or the patient's management of the medicine contained in the pen device 10. In the example illustrated in FIG. 2D, a high temperature alert for the medicine in the pen device 10 is signaled on the display screen of the software application user interface, e.g., in which the high temperature alert may indicate that the medicine could have lost its effectiveness.

FIG. 2E shows an example of a user interface display for exemplary remote notifications. For example, the exemplary notifications can be provided via text messages, email, or other types of communications that provide certain patient data to parents or caregivers to allow them to monitor the patient's therapy management remotely.

FIG. 2F shows an example of a user interface display for exemplary user verification or override of the determined dose type by the dose distinguisher module. For example, after a dose is displayed in the history screen (e.g., manually entered or automatically communicated by the pen 10), the user can select a displayed individual dispensed dose by pressing on its row entry in the table of the history interface. After being selected, an exemplary GUI screen (such as that shown in FIG. 2F) with the dose/prime selection pops up as an overlay allowing the user to then select which type of dose that entry should be. For example, if the entry was changed from the original determined type, the history display and record are updated with the new user selection.

In some implementations, for example, the system may allow both automatic as well as manual logging of doses. In such cases, the system can include a dose duplication checking feature included in the software application of the companion device 5 to check for duplicate manual and automatically transferred dose data inputs to the companion device 5. In an example, the user could manually log a dose which has been automatically logged due to misunderstanding or other factors. For example, if the system sees multiple doses of the same size or similar size logged by different methods (manually and automatically) within a small period of time (e.g., such as 1 to 5 or 10 minutes, or other set time frame), then the system could assume they are duplicates and automatically delete one of the doses.

In some embodiments, the pen device 10 can include a light to emit light from the pen device 10. The emitted light can be automatically produced by the pen device 10 based on a received control signal from the companion device 5 (or, for example, from a data processing unit of the pen device 10) to provide a reminder to the user that he/she has or has not taken the medication based on a schedule or dose tracking program (e.g., such as insulin). The emitted light may also serve as an indicator of active insulin on board. For example, if the user's active insulin time is set to 5 hours, then the light could be lit for 5 hours after each dose. If the light was out, the user would know immediately that they had not dosed in some time and had no active insulin. If the light was lit, they would know that they had active insulin and must take it into account during any dose calculations being made. In some embodiments, for example, the signal could be through haptic feedback where a single vibration or series of vibrations over time possibly via vibratory motor and could indicate IOB, dosing, alarms, or a combination thereof.

Exemplary Embodiments of the Pen Device 10

Figure 4:
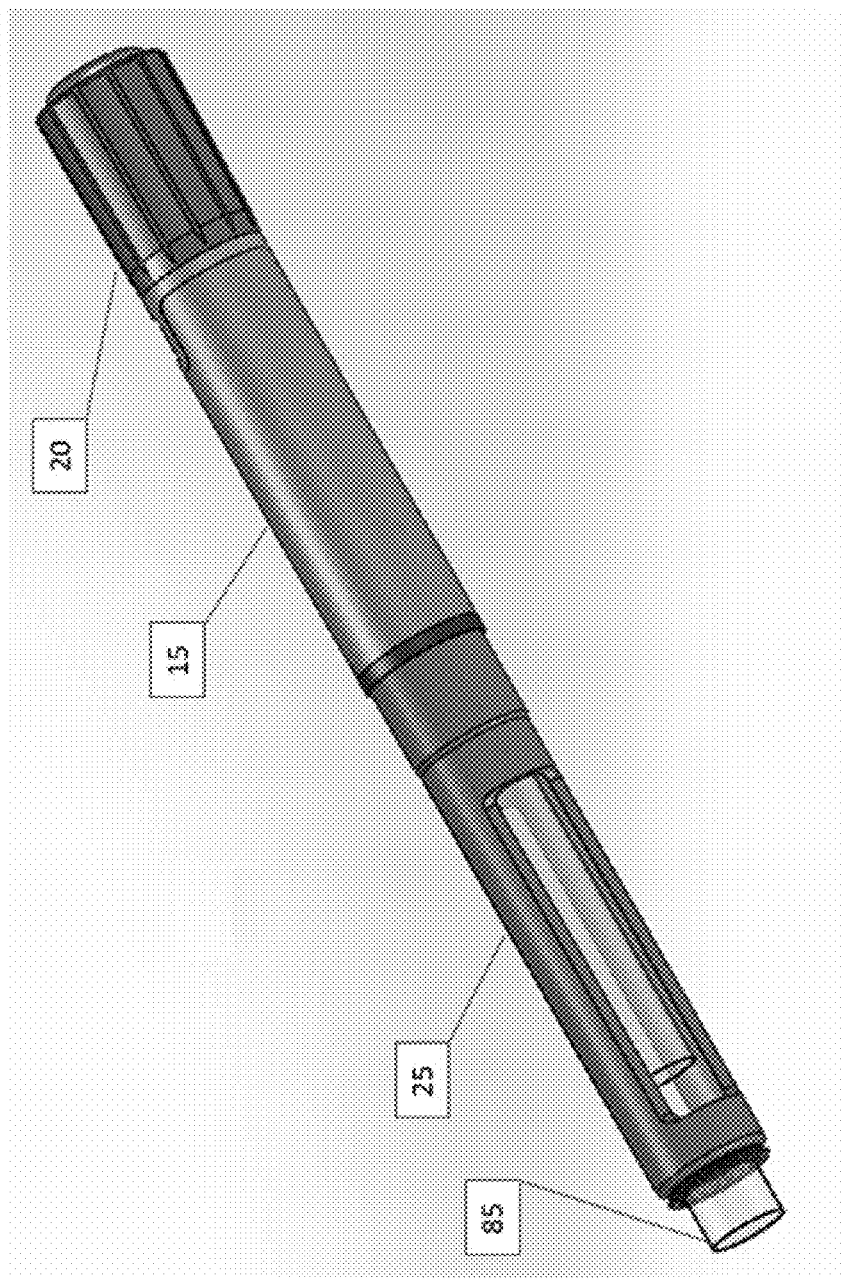
FIGS. 4 and 5 show schematic diagrams of an exemplary embodiment of a pen device of the disclosed technology.
Figure 5:
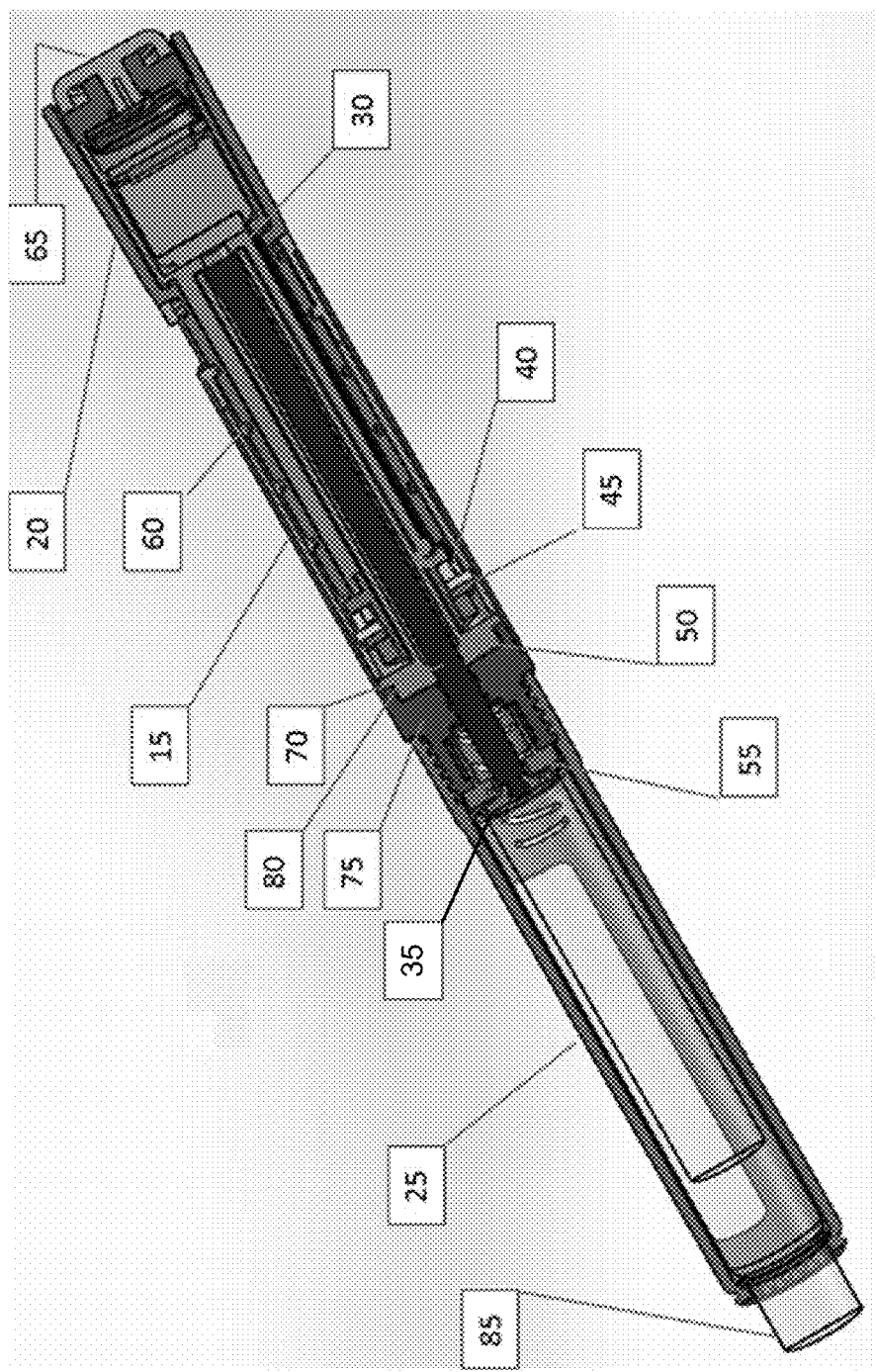

FIGS. 4 and 5 show schematic illustrations of exemplary embodiments of the pen device 10. Turning now to FIGS. 4 and 5, the overall operation is that a mechanism is provided to force a displacement of a piston which resides within a medicament vial or cartridge 85. The displacement of the piston of the medicament vial 85 forces a volume of the medicament (that is proportional to the displacement of the piston) out of the vial 85, e.g., allowing it to be injected into a patient. The vial 85 is held within a medicament housing 25 of the pen device 10. The medicament housing 25 attaches to a main body housing 15 of the pen device 10, which includes a dose setting and dispensing mechanism and electronics unit of the pen device 10. In some embodiments, for example, the medicament housing 25 and the main body housing 15 may be a singular housing structure. The medicament housing 25 is structured to include a chamber to hold and/or encase the medicament vial 85 within the housing 25 of the pen device 10. The pen device 10 can also include a detachable pen cap (not shown) to cover an end of the pen device 10 that exposes a needle assembly (not shown) of the pen device 10 to disburse the medicine out of the pen device 10 when dispensed from the vial 85. The pen device 10 can include a vial spring 35, which provides a force on a screw retractor 55 to push the medicament vial 85 into the medicament housing 25 to ensure good dose accuracy. The pen device 10 includes a dose knob 20 attached to or included as part of the housing 15, where the dose knob is coupled to the housing by a non-self-locking thread 60. In some embodiments, for example, an electronics housing 30 may reside within the dose knob 20, in which the electronics housing 30 contains the electronics unit of the pen device 10. The dose setting mechanism includes a dose knob 20. When the dose knob 20 is rotated into or out of the housing 15 to adjust the dose, the electronics housing 30 does not turn. However, when translational or axial force is placed to the dose button 65 (e.g., in which resides the electronics housing), a catch structure component is engaged to lock the electronics housing 30 and dose knob 20 together, forcing them to rotate together as the pair travel back into the housing 15 upon actuation of the dose dispensing mechanism to apply force to the dose knob 20 to cause dispensing of the set dose. The rotation of the dose knob 20, e.g., which can be via the electronics housing 30, rotates a shaft 50 (e.g., which can be configured as a bi-directional clutch shaft). The shaft 50 in turn rotates a dose screw 70 which rides within a nut 75 which is fixed to the housing 15. This rotation causes the dose screw 70 to extend out of the housing 15 causing an injection of medicament. In some embodiments, for example, the dose dispensing mechanism can include a friction-causing structure 80, e.g., which can be coupled to the exemplary bi-directional clutch shaft 50 to present a frictionous surface (i.e., a surface that provides friction) to make contact with the nut 75 or housing body 15 or other internal structure of the dose dispensing mechanism, which acts from the bi-directional clutch shaft 50 to the housing 15 or nut 75 to prevent rotation of the shaft 50 while the dose setting mechanism is being adjusted via turning of the dose knob 20, but also allowing the friction to be overcome during the dose dispensing operation. In addition, by overcoming friction in the opposite direction the dose screw 70 may be driven back into the housing 15 and prepared for a new cartridge of medicament to be loaded. In some embodiments, for example, the pen device 10 includes a screw retractor component 55 that is axially fixed to the housing but rotationally free. The screw retractor component 55 is operable to be bent in to "grab" the non-circular cross section of the dose screw 70 allowing it to be rotated relative to the housing 15 and driven back into the housing 15. In some implementations, for example, the components of the pen device 10 could be manufactured by injection molding, machining or other similar process. In embodiments including the bi-directional clutch shaft, for example, the pen device 10 is capable of allowing retraction of the lead screw, and repeatability of operation of the dose dispensing mechanism.

In some embodiments, the sensor unit of the pen device 10 includes a rotational encoder, for example, between the dose knob 20 (e.g., which can be coupled to the jack screw) and the housing 15, and in electrical communication with the electronics unit contained in the electronics housing 30. The encoder is included in a sensor unit to determine the quantity of the dose set by the dose setting mechanism, and/or, the quantity of the dose dispensed by the dose dispensing mechanism. In some implementations, for example, the encoder can be configured in the pen device 10 to determine the dispensed dose by detecting rotation of the lead screw which is correlated with displacement of the pusher foot which is correlated with displacement of the receiving plunger in the vial 85, which in turn is correlated with dispensed insulin. In some embodiments, for example, the encoder can include two flat plates with contacts in between them. The plates are aligned perpendicular to the axis of the device. For one plate, a contact plate 40 is rotationally fixed to the jack screw, e.g., which can be via the electronics housing 30; and for the other plate, a code wheel 45 is rotationally fixed to the housing 15. In implementations, for example, when relative motion occurs between these two plates during dosing, the relative motion is measured and transmitted to the data processing and communications unit for processing, storage and/or transmission to the companion device 5.

In some embodiments of the pen device 10, for example, the dose setting and dispensing mechanism may include a mechanism in which the dose screw 70 is comprised of an elongate nut which screws in and out of the housing to provide dosing. The nut component in the previous described embodiment (e.g., nut 75) can include a separate screw structure; whereas in this embodiment of the dose screw, the nut component is part of the dose screw including exterior threads and is coupled to the housing 15. When the exemplary bi-directional clutch shaft 50 provides rotation, it operates on the jack screw, e.g., in which the dosing nut in this case threading it out of the housing.

Exemplary Implementations of Companion Device

In some implementations of the companion device 5, for example, the software application can include data processing algorithms stored as executable code in the memory of the data processing unit of the companion device 5 and an executable user interface to be provided to assist the user in determining the size of the dose they require. One exemplary algorithm includes a dose calculator or suggestion algorithm. Typical inputs to the dose calculator algorithm can include current blood glucose as well as carbohydrate content that the user intends to eat. For example, these can be inputs can be received on the companion device 5 via the user interface by providing up and down arrows or a numeric keypad. A slider could be used to allow the user to quickly achieve the desired input value. In addition, plus and minus keys (e.g., or up and down keys) could be provided to fine tune the information entered on the slider if need be. In addition, dynamic scaling of the slider could be implemented where the historical inputs are used to determine a likely maximum and minimum range for the slider. For example, if the user has entered carbohydrate content from 20 to 80 grams, then the slider could use 20 g as the low end and 80 g as the upper end, or it could add some margin for example allowing 20 to 90 grams to be entered. In this way, for example, the companion device 5 tailors itself to the needs of the patient.

In order to verify the existing bonding or pairing of the pen device 10 to the companion device 5 and ensure that the correct pen is bonded or paired with the device 5 (e.g., smartphone), in some embodiments, the companion device 5 could ask the user to dose a particular dose from the pen. The user would then dial in and deliver whatever dose was requested. This would provide a level of certainty that both the companion device and pen were under control of the user and prevent inadvertent pairing.

Because it is desired to know when a cartridge is replaced, it is possible to interpret the encoder signal to label a cartridge replacement. In some implementations, for example, the encoder may be a full quadrature encoder which can detect movement in both directions (and differentiate between them). However, detecting a cartridge replacement is not as easy as detecting rearward motion because there can be some rearward motion at any time. The data processing unit can be programmed to process all rearward motion detected by the exemplary full quadrature encoder within a time period (e.g., 1 second to 2 minutes) to be summed, and if the total is over a threshold (e.g., 50 units), then the event be labeled a cartridge replacement.

In the companion device 5 a simplified set of timed parameters may be utilized. In one example implementation, for example, four timed periods are predetermined (e.g., breakfast, lunch, dinner and bedtime). The time of each event is entered into a screen. Each of the clinical variables (e.g., carbohydrate factor, correction factor, target blood glucose, etc.) can then be entered for each time period. Implementations of the timed parameters may greatly speed the operations of the system.

FIG. 6A shows a diagram of an exemplary method to classify a dose of medicine dispensed from an injection pen. The method includes a process 602 to detect one or more doses of medicine dispensed from an injection pen device and time data associated with the one or more dispensed doses to generate dose data corresponding to dispensing events. The method includes a process 604 to process the dose data corresponding to one or more dispensing events over a predetermined duration of time to form a dose dispensing sequence. The method includes a process 606 to determine a type of dispensing event as a priming event or an injection event for the dose data in the dose dispensing sequence by assigning a last dispensing event in the dose dispensing sequence as the injection event and any previous dispensing events in the dose dispensing sequence as the priming events.

Implementations of the method shown in FIG. 6A can optionally include the following exemplary features. For example, in some implementations, the method can further include detecting force signal data applied at a dispensing portion of the injection pen device; detecting force time data associated with the force data; processing the detected force signal data and force time data to determine physical contact between the dispensing portion and a body based on a predetermined force threshold; comparing the force time data associated with determined physical contact to the time data associated with the last dispensing event; and determining that the type of dispensing event of the last dispensing event is the injection dose if the force time data associated with determined physical contact corresponds to the time data associated with the last dispensing event, or determining that the type of dispensing event of the last dispensing event is a priming event if the force time data associated with determined physical contact does not correspond to the time data associated with the last dispensing event. In some implementations, for example, the method can further include comparing the amount of the dispensed doses for each of the dispensing events in the dose dispensing sequence to a predetermined dose quantity threshold; and determining the type of dispensing event for a dispensed dose having its amount larger than the predetermined dose quantity threshold and the largest amongst the compared dispensing events as the injection event.

FIG. 6B shows a diagram of another exemplary method to classify a dose of medicine dispensed from an injection pen. The method includes a process 652 to detect one or more doses of medicine dispensed from an injection pen device and time data associated with the one or more dispensed doses to generate dose data corresponding to dispensing events, in which the detecting includes sensing a rate at which the medicine is dispensed from the injection pen device. The method includes a process 654 to process the dose data corresponding to one or more dispensing events over a predetermined duration of time to form a dose dispensing sequence. The method includes a process 656 to compare the rate of the one or more dispensed doses for each of the dispensing events in the dose dispensing sequence to a predetermined dispensing rate threshold. The method includes a process 658 to determine a type of dispensing event as a priming event for a dispensing event in the dose dispensing sequence when the corresponding sensed rate is slower than the predetermined dispensing rate threshold, and to determine the type of dispensing event as an injection event for a dispensing event in the dose dispensing sequence when the corresponding sensed rate is faster than the predetermined dispensing rate threshold.

Examples

The following examples are illustrative of several embodiments of the present technology. Other exemplary embodiments of the present technology may be presented prior to the following listed examples, or after the following listed examples.

In one example of the present technology (example 1), a system for administering a medicine to a patient includes an injection pen device and a mobile communication device in wireless communication with the injection pen. The injection pen device includes a housing including a main body structured to include a chamber to encase a cartridge containing medicine when the cartridge is loaded in the chamber, a dose setting and dispensing mechanism to set and dispense a particular dose of the medicine from the loaded cartridge, the dose setting and dispensing mechanism including a dose knob, a shaft, and a piston assembly including a plunger, in which the dose knob is rotatable to cause the shaft to move to a position proportional to a set dose of the medicine, and in which the dose knob is translationally moveable to cause the shaft to drive the plunger to push against the cartridge to dispense the medicine from the cartridge, a sensor unit to detect a dispensed dose based on one or both of positions and movements of the dose setting and dispensing mechanism, in which the dispensed dose includes an amount of medicine dispensed from the cartridge, and an electronics unit in communication with the sensor unit, the electronics unit including a processing unit including a processor and memory to process the detected dispensed dose and time data associated with a dispensing event to generate dose data, a transmitter to wirelessly transmit the dose data to a user's device, and a power source to provide electrical power to the electronics unit. The mobile communication device includes a data processing unit including a processor to process the dose data and a memory to store or buffer the dose data, a display to present a user interface to the user, and a wireless communications unit to wirelessly receive the dose data from the injection pen device.

Example 2 includes the system as in example 1, in which the medicine includes insulin, an infertility treatment drug, or a pain treatment drug.

Example 3 includes the system as in example 1, in which the time data includes a specific time of occurrence of the dispensing event, or a relative time associated with a beginning, a duration, and/or a conclusion of the dispensing event.

Example 4 includes the system as in example 1, in which the housing of the injection pen device further includes a detachable cap to cover an end of the injection pen device including a needle assembly to dispense the medicine received from the cartridge.

Example 5 includes the system as in example 1, in which the plunger of the injection pen device is operable to be moved by the shaft such that the plunger pushes against a piston of the cartridge to cause the piston to move a certain distance that is proportional to the set dose of the medicine to dispense the medicine from the cartridge.

Example 6 includes the system as in example 1, in which the shaft of the injection pen device includes and a bi-directional clutch shaft.

Example 7 includes the system as in example 6, in which the plunger of the piston assembly includes a screw component contained within the bi-directional clutch shaft, and the piston assembly includes a nut component fixed to the main body of the housing, in which movement of the bi-directional clutch shaft causes the screw component to rotate a screw within the nut component and extend out of the main body to make contact against a moveable surface of the piston of the medicine cartridge.

Example 8 includes the system as in example 7, in which the bi-directional clutch shaft of the injection pen device includes a frictionous surface in contact with the main body housing or the nut component and capable of preventing rotation of the bi-directional clutch shaft when the dose knob is being rotated to set the dose.

Example 9 includes the system as in example 1, in which the sensor unit of the injection pen device is operable to detect the set dose based on one or both of positions and movements of the dose setting and dispensing mechanism.

Example 10 includes the system as in example 1, in which the sensor unit and the data processing and communication unit of the injection pen device are housed in a housing compartment located in the dose knob, in which the housing compartment does not move with the rotation of the dose knob when the dose is being set by the dose setting and dispensing mechanism, and the housing compartment does move with the dose knob when the dose is being dispensed by the dose setting and dispensing mechanism.

Example 11 includes the system as in example 10, in which the housing compartment of the injection pen device includes a catch component operable to only couple the housing compartment to the dose knob when the dose setting and dispensing mechanism is being operated to dispense the dose.

Example 12 includes the system as in example 1, in which the transmitter of the injection pen device is operable to wirelessly transmit the dose data to the mobile communication device using a Bluetooth, a WiFi, or a ZigBee wireless transmission.

Example 13 includes the system as in example 1, in which the mobile communication device includes a smartphone, a tablet, a wearable computing device including a smartwatch or smartglasses, a computer including a laptop or a desktop computer, or one or more computers networked in a communication network through the Internet.

Example 14 includes the system as in example 1, in which the injection pen further includes a temperature sensor operable to detect temperature at or near medicine cartridge, the temperature sensor in communication with the signal processing unit to receive the detected temperature.

Example 15 includes the system as in example 1, in which the injection pen device further includes an operation sensor to detect when the dose setting and dispensing mechanism is being operated.

Example 16 includes the system as in example 1, in which the dose dispensing mechanism is a motorized mechanism.

Example 17 includes the system as in example 1, in which the processing unit of the injection pen device or the mobile communication device includes a software application program product comprising a non-transitory computer-readable storage medium stored in the memory of the data processing unit of the mobile communication device and having instructions stored thereon and operable to cause the mobile communication device to perform operations, including processing one or more dose data corresponding to one or more dispensing events over a predetermined duration of time to form a dose dispensing sequence; and determining a type of dispensing event as a priming event or an injection event for the one or more dose data in the dose dispensing sequence, in which the determining includes assigning the last dispensing event in the dose dispensing sequence as the injection event and any previous dispensing events in the dose dispensing sequence as the priming events.

Example 18 includes the system as in example 17, in which the injection pen device further includes a sensor to detect external force signals applied to a needle assembly of the injection pen device that indicate contact of the injection pen device with the user, and in which the software application program product further includes instructions to cause the mobile communication device to perform: processing the detected external force signals to determine the presence of contact to the needle assembly with corresponding time information of the last dispensing event; and determining the type of dispensing event of the last dispensing event is the injection dose if there was the presence of contact detected, or determining the type of dispensing event of the last dispensing event is the priming event if there was no presence of contact detected.

Example 19 includes the system as in example 17, in which the software application program product further includes instructions to cause the mobile communication device to perform: if a single dispensing event occurs in the predetermined duration of time, identifying the single dispensing event as a priming event; or comparing the amount of the dispensed doses for each of the dispensing events in the dose dispensing sequence to a predetermined dose quantity threshold, and determining the type of dispensing event for a dispensed dose having its amount larger than the predetermined dose quantity threshold and the largest amongst the compared dispensing events as the injection event.

Example 20 includes the system as in example 17, in which the sensor unit is operable to detect a rate at which the medicine is dispensed from the cartridge, and in which the software application program product further includes instructions to cause the mobile communication device to perform: comparing the rate of the dispensed doses for each of the dispensing events in the dose dispensing sequence to a predetermined dispensing rate threshold, and determining the type of dispensing event for a dispensed dose having its detected rate slower than the predetermined dispensing rate threshold.

Example 21 includes the system as in example 1, in which the data processing unit of the mobile communication device is operable to process the dose data to determine information about the user's health, and in which one or both of the injection pen device and the mobile communication device include a visual, auditory, or haptic signaling unit to produce an alert based on the processed dose data.

Example 22 includes the system as in example 1, in which the injection pen device includes a software application program product comprising a non-transitory computer-readable storage medium stored in the memory of the processing unit of the injection pen device and having instructions stored thereon and operable to cause the injection pen device to perform operations to communicatively unbond the injection pen device from a first mobile communication device of the user to which the injection pen device is communicatively bonded, including detecting a pattern sequence of operations of the dose setting and dispensing mechanism in a predetermined time frame, in which the pattern sequence includes setting the dose setting and dispensing mechanism to or greater than a first level and operating the dose setting and dispensing mechanism to dispense a dose; initiating a count of the predetermined time frame when the dose setting and dispensing mechanism is set or greater than at a particular first level; and clearing encryption keys stored in the processing unit of the injection pen device associated with the first mobile communication device when the pattern sequence is detected in the predetermined time.

In one example of the present technology (example 23), a method to classify a dose of medicine dispensed from an injection pen includes detecting one or more doses of medicine dispensed from an injection pen device and time data associated with the one or more dispensed doses to generate dose data corresponding to dispensing events; processing the dose data corresponding to one or more dispensing events over a predetermined duration of time to form a dose dispensing sequence; and determining a type of dispensing event as a priming event or an injection event for the dose data in the dose dispensing sequence by assigning a last dispensing event in the dose dispensing sequence as the injection event and any previous dispensing events in the dose dispensing sequence as the priming events.

Example 24 includes the method as in example 23, further including detecting force signal data applied at a dispensing portion of the injection pen device; detecting force time data associated with the force data; processing the detected force signal data and force time data to determine physical contact between the dispensing portion and a body based on a predetermined force threshold; comparing the force time data associated with determined physical contact to the time data associated with the last dispensing event; and determining that the type of dispensing event of the last dispensing event is the injection dose if the force time data associated with determined physical contact corresponds to the time data associated with the last dispensing event, or determining that the type of dispensing event of the last dispensing event is a priming event if the force time data associated with determined physical contact does not correspond to the time data associated with the last dispensing event.

Example 25 includes the method as in example 23, further including comparing the amount of the dispensed doses for each of the dispensing events in the dose dispensing sequence to a predetermined dose quantity threshold; and determining the type of dispensing event for a dispensed dose having its amount larger than the predetermined dose quantity threshold and the largest amongst the compared dispensing events as the injection event.

In one example of the present technology (example 26), a method to classify a dose of medicine dispensed from an injection pen includes detecting one or more doses of medicine dispensed from an injection pen device and time data associated with the one or more dispensed doses to generate dose data corresponding to dispensing events, in which the detecting includes sensing a rate at which the medicine is dispensed from the injection pen device; processing the dose data corresponding to one or more dispensing events over a predetermined duration of time to form a dose dispensing sequence; comparing the rate of the one or more dispensed doses for each of the dispensing events in the dose dispensing sequence to a predetermined dispensing rate threshold; and determining a type of dispensing event as a priming event for a dispensing event in the dose dispensing sequence when the corresponding sensed rate is slower than the predetermined dispensing rate threshold, and determining the type of dispensing event as an injection event for a dispensing event in the dose dispensing sequence when the corresponding sensed rate is faster than the predetermined dispensing rate threshold.

In one example of the present technology (example 27), a method of unbonding an injection pen device from a mobile communication device includes providing instructions to a user of the injection pen device that has been communicatively bonded to a first mobile communication device to perform an operation sequence including two or more operations of the injection pen device in a predetermined time frame; initiating, by a processing unit of the injection pen device, a count of the predetermined time frame once a dose setting mechanism of the injection pen device is set at or greater than a first level; detecting, by the injection pen device, operations of the dose setting and a dose dispensing mechanism of the injection pen device; and clearing encryption keys stored in the processing unit of the injection pen device associated with the first mobile communication device when the operation sequence is detected within the predetermined time.

Example 28 includes the method as in example 27, in which the instructions include operating a dose setting mechanism of the injection pen device to the first level or greater than the first level, operating the dose setting mechanism to a second level less than the first level, operating the dose setting mechanism to a third level greater than the second level, operating the dose setting mechanism to a fourth level less than the third level, and operating a dose dispensing mechanism of the injection pen.

Example 29 includes the method as in example 27, in which the providing instructions includes displaying the instructions to the user on a display screen of a second mobile communication device to perform the two or more operations of the injection pen device.

Example 30 includes the method as in example 27, further including initiating, by a second mobile communication device, a bonding sequence to communicatively bond the second mobile communication device with the injection pen device; prompting the user, at the display screen of the second mobile communication device, to enter a bond code into the second mobile communication device; receiving, at the second mobile communication device, the user-entered bond code; and providing, at the second mobile communication device, encryption keys to the injection pen device and the second mobile communication device.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A system for administering a medicine to a patient, comprising:
an injection device, comprising:
a housing including a main body structured to include a chamber to encase a cartridge containing medicine upon loading of the cartridge in the chamber;
a dose setting and dispensing mechanism to set and dispense a particular dose of the medicine from the cartridge, the dose setting and dispensing mechanism including a dose knob, a shaft, and a plunger, wherein the dose knob is rotatable to cause the shaft to move to a position proportional to a set dose of the medicine, and wherein the dose knob is moveable to cause the shaft to drive the plunger to dispense the medicine from the cartridge;
a sensor to detect a dispensed dose, wherein the dispensed dose includes an amount of medicine dispensed from the cartridge, and
an electronics unit in communication with the sensor unit, the electronics unit including a processor and a non-transitory memory to process the detected dispensed dose and time data associated with a dispensing event to generate dose data, a transmitter to wirelessly transmit the dose data to a user device, and a power source to provide electrical power to the electronics unit; and
a mobile communication device in wireless communication with the injection device, wherein the mobile communication device includes a processor to process the dose data and a memory to store or buffer the dose data, a display, and a wireless communications unit to wirelessly receive the dose data from the injection device, wherein the processor includes a software application program product stored in the memory of the mobile communication device including instructions operable to cause the mobile communication device to perform operations comprising:
processing one or more dose data corresponding to one or more dispensing events to form a dose dispensing sequence, wherein
the dose dispensing sequence is formed such that the dispensing events of the dose disposing sequence all occur in temporal proximity of one another that span less than a predetermined temporal threshold, and
the last dispensing event in the dose dispensing sequence is always identified as the injection event and one or more of the dispensing events other than the last dispensing events in the dose dispensing sequence are identified as the priming events, wherein the injection device includes a software application program product stored in the memory of the processing unit of the injection device and includes instructions operable to cause the injection device to perform operations to communicatively unbond the injection device from the mobile communication device to which the injection device is communicatively bonded, comprising:

detecting a pattern sequence of operations of the dose setting and dispensing mechanism in a predetermined time frame; and clearing encryption keys stored in the memory of the injection device associated with the mobile communication device when the pattern sequence is detected in the predetermined time frame.

2. The system of claim 1, wherein the predetermined temporal threshold is one of: 10 seconds or 30 seconds.

3. The system of claim 1, wherein the medicine includes insulin, or an infertility treatment drug.

4. The system of claim 1, wherein the time data includes a specific time of occurrence of the dispensing event, or a relative time associated with a beginning, a duration, or a conclusion of the dispensing event.

5. The system of claim 1, wherein the software application program product stored in the memory of the mobile communication device further includes instructions operable to receive a user verification input indicative of whether a dispensed dose corresponds to a priming event.

6. The system of claim 1, wherein the housing of the injection device further includes a detachable cap to cover an end of the injection device including a needle assembly to dispense the medicine received from the cartridge.

7. The system of claim 1, wherein the shaft of the injection device includes a bi-directional clutch shaft.

8. The system of claim 7, wherein the plunger includes a screw component contained within the bi-directional clutch shaft, and the dose setting and dispensing mechanism includes a nut component fixed to the main body of the housing, wherein movement of the bi-directional clutch shaft causes the screw component to rotate a screw within the nut component and extend out of the main body to push against the medicine cartridge.

9. The system of claim 1, wherein the transmitter of the injection device is operable to wirelessly transmit the dose data to the mobile communication device using a Bluetooth or Bluetooth Low Energy transmission protocol.

10. The system of claim 1, wherein the mobile communication device includes one or more of the following devices: a smartphone, a tablet, a wearable computing device including a smartwatch or smartglasses, a computer including a laptop or a desktop computer, or one or more computers networked in a communication network through the Internet.

11. The system of claim 1, wherein the injection device further includes a temperature sensor operable to detect temperature at or near the medicine cartridge, the temperature sensor in communication with the processor of the injection device to communicate the detected temperature.

12. The system of claim 1, wherein the injection device further includes an operation sensor to detect when the dose setting and dispensing mechanism is being operated.

13. The system of claim 1, wherein the dose dispensing mechanism is a motorized mechanism.

14. The system of claim 1, wherein the processor of the mobile communication device is operable to process the dose data to determine information about a user's health or a value of insulin on board (IOB), and wherein one or both of the injection device or the mobile communication device include a visual, auditory, or haptic signaling unit to produce an alert based on the processed dose data or an indication of the IOB.

15. The system of claim 1, wherein the software application program product stored in the memory of the mobile communication device includes instructions stored thereon operable to cause the mobile communication device to generate a drug confusion alert indicative of (a) a potential drug interaction or (b) an incorrect delivery of the drug in response to a comparison of a particular injection event with one or both of an electronic medical record or a physician order.

16. The system of claim 1, wherein the mobile communication device further includes a camera communicatively connected to the data processing unit of the mobile communication device, the camera to capture an image of a bar code on the cartridge to enable processing of the barcode data by the processor of the mobile communication device and identification of the medicine in the cartridge.

17. The system of claim 1, wherein the software application program product stored in the memory of the mobile communication device includes instructions stored thereon operable to cause the mobile communication device to generate a maximum dose setting alarm indicative that a maximum dosage of a particular medicine for a particular user has been reached.

18. The system of claim 1, wherein the medicine includes glucagon.

19. The system of claim 18, wherein the software application program product stored in the memory of the mobile communication device includes instructions stored thereon operable to cause the mobile communication device to determine or set a glucagon dose.

20. The system of claim 18, wherein glucagon dose is set or determined in accordance with a glucagon factor and a particular rise in blood glucose level.

21. The system of claim 1, wherein the medicine includes a pain treatment drug.

22. The system of claim 1, wherein the dose setting and dispensing mechanism includes a screw component, and
the injection device includes a software application program product stored in the memory of the injection device and includes instructions operable to detect a replacement of the cartridge based on detection of a movement of the screw component in a particular direction for more than a predetermined number of units.

23. The system of claim 1, wherein the injection device is a medicament pen device.

24. A system for administering a medicine to a patient, comprising:
an injection device, comprising:
a housing including a main body structured to include a chamber to encase a cartridge containing medicine upon loading of the cartridge in the chamber;
a dose setting and dispensing mechanism to set and dispense a particular dose of the medicine from the cartridge, the dose setting and dispensing mechanism including a dose knob, a shaft, and a plunger, wherein the dose knob is rotatable to cause the shaft to move to a position proportional to a set dose of the medicine, and wherein the dose knob is moveable to cause the shaft to drive the plunger to dispense the medicine from the cartridge;
a sensor to detect a dispensed dose, wherein the dispensed dose includes an amount of medicine dispensed from the cartridge, and
an electronics unit in communication with the sensor unit, the electronics unit including a processor and a non-transitory memory to process the detected dispensed dose and time data associated with a dispensing event to generate dose data, a transmitter to wirelessly transmit the dose data to a user device, and a power source to provide electrical power to the electronics unit; and
a mobile communication device in wireless communication with the injection device, wherein the mobile communication device includes a processor to process the dose data and a memory to store or buffer the dose data, a display, and a wireless communications unit to wirelessly receive the dose data from the injection device, wherein the processor includes a software application program product stored in the memory of the mobile communication device including instructions operable to cause the mobile communication device to perform operations comprising:
processing one or more dose data corresponding to one or more dispensing events to form a dose dispensing sequence, wherein
the dose dispensing sequence is formed such that the dispensing events of the dose disposing sequence all occur in temporal proximity of one another that span less than a predetermined temporal threshold, and
the last dispensing event in the dose dispensing sequence is always identified as the injection event and one or more of the dispensing events other than the last dispensing events in the dose dispensing sequence are identified as the priming events, wherein the shaft of the injection device includes a bi-directional clutch shaft and the bi-directional clutch shaft of the injection device includes a surface in contact with the main body housing or the nut component and capable of preventing rotation of the bi-directional clutch shaft when the dose knob is being rotated to set the dose.

25. A system for administering a medicine to a patient, comprising:
an injection device, comprising:
a housing including a main body structured to include a chamber to encase a cartridge containing medicine upon loading of the cartridge in the chamber;
a dose setting and dispensing mechanism to set and dispense a particular dose of the medicine from the cartridge, the dose setting and dispensing mechanism including a dose knob, a shaft, and a plunger, wherein the dose knob is rotatable to cause the shaft to move to a position proportional to a set dose of the medicine, and wherein the dose knob is moveable to cause the shaft to drive the plunger to dispense the medicine from the cartridge;
a sensor to detect a dispensed dose, wherein the dispensed dose includes an amount of medicine dispensed from the cartridge, and
an electronics unit in communication with the sensor unit, the electronics unit including a processor and a non-transitory memory to process the detected dispensed dose and time data associated with a dispensing event to generate dose data, a transmitter to wirelessly transmit the dose data to a user device, and a power source to provide electrical power to the electronics unit; and
a mobile communication device in wireless communication with the injection device, wherein the mobile communication device includes a processor to process the dose data and a memory to store or buffer the dose data, a display, and a wireless communications unit to wirelessly receive the dose data from the injection device, wherein the processor includes a software application program product stored in the memory of the mobile communication device including instructions operable to cause the mobile communication device to perform operations comprising:

processing one or more dose data corresponding to one or more dispensing events to form a dose dispensing sequence, wherein the dose dispensing sequence is formed such that the dispensing events of the dose disposing sequence all occur in temporal proximity of one another that span less than a predetermined temporal threshold, and the last dispensing event in the dose dispensing sequence is always identified as the injection event and one or more of the dispensing events other than the last dispensing events in the dose dispensing sequence are identified as the priming events, wherein the sensor unit, the processor and the memory, and the transmitter of the injection device are housed in a housing compartment located in the dose knob, wherein the housing compartment does not move with the rotation of the dose knob when the dose is being set by the dose setting and dispensing mechanism, and the housing compartment does move with the dose knob when the dose is being dispensed by the dose setting and dispensing mechanism.

26. A system for administering a medicine to a patient, comprising:

an injection device, comprising:
- a housing including a main body structured to include a chamber to encase a cartridge containing medicine upon loading of the cartridge in the chamber;
- a dose setting and dispensing mechanism to set and dispense a particular dose of the medicine from the cartridge, the dose setting and dispensing mechanism including a dose knob and a shaft, wherein the dose knob is rotatable to cause the shaft to move to set the particular dose of the medicine;
- a sensor to detect a dispensed dose, wherein the dispensed dose includes an amount of medicine dispensed from the cartridge, and
- an electronics unit in communication with the sensor unit, the electronics unit including a processor and a non-transitory memory to process the detected dispensed dose and time data associated with a dispensing event to generate dose data, a transmitter to wirelessly transmit the dose data to a user device, and a power source to provide electrical power to the electronics unit; and a mobile communication device in wireless communication with the injection device, wherein the mobile communication device includes a processor to process the dose data and a memory to store or buffer the dose data, a display, and a wireless communications unit to wirelessly receive the dose data from the injection device, wherein the processor includes a software application program product stored in the memory of the mobile communication device including instructions operable to cause the mobile communication device to perform operations comprising:

processing one or more dose data corresponding to one or more dispensing events to form a dose dispensing sequence and to identify one of the dispensing events the dose dispensing sequence as the injection event and one or more of the dispensing event in the dose dispensing sequence as the priming events, wherein the injection device includes a software application program product stored in the memory of the processing unit of the injection device and includes instructions operable to cause the injection device to perform operations to communicatively unbond the injection device from the mobile communication device to which the injection device is communicatively bonded, comprising:

detecting a pattern sequence of operations of the dose setting and dispensing mechanism in a predetermined time frame; and clearing encryption keys stored in the memory of the injection device associated with the mobile communication device when the pattern sequence is detected in the predetermined time frame.

* * * * *